(12) United States Patent
Gill et al.

(10) Patent No.: US 10,183,962 B2
(45) Date of Patent: Jan. 22, 2019

(54) **SYNTHETIC OLIGOMERS OF *NEISSERIA MENINGITIS* SEROGROUP X AND PROCESS OF PREPARING THEM**

(71) Applicant: MSD WELLCOME TRUST HILLEMAN LABORATORIES PVT. LTD., New Delhi (IN)

(72) Inventors: Davinder Gill, New Delhi (IN);
Kishore Harale, New Delhi (IN);
Manoj Kumar Chhikara, Delhi (IN)

(73) Assignee: MSD WELLCOME TRUST HILLEMAN LABORATORIES PVT. LTD., New Delhi (IN)

( * ) Notice: Subject to any disclaimer, the term of this patent is extended or adjusted under 35 U.S.C. 154(b) by 10 days.

(21) Appl. No.: 15/119,880

(22) PCT Filed: Feb. 24, 2015

(86) PCT No.: PCT/IB2015/051370
§ 371 (c)(1),
(2) Date: Aug. 18, 2016

(87) PCT Pub. No.: WO2015/128797
PCT Pub. Date: Sep. 3, 2015

(65) Prior Publication Data
US 2017/0066794 A1    Mar. 9, 2017

(30) Foreign Application Priority Data

Feb. 25, 2014 (IN) .............................. 526/DEL/2014

(51) Int. Cl.
| | | |
|---|---|---|
| *C07H 15/04* | (2006.01) |
| *C07H 11/04* | (2006.01) |
| *C08B 37/00* | (2006.01) |
| *C07H 15/12* | (2006.01) |
| *C07H 1/00* | (2006.01) |
| *C07H 1/02* | (2006.01) |

(52) U.S. Cl.
CPC ............... *C07H 15/04* (2013.01); *C07H 1/00* (2013.01); *C07H 1/02* (2013.01); *C07H 11/04* (2013.01); *C07H 15/12* (2013.01); *C08B 37/0009* (2013.01)

(58) Field of Classification Search
None
See application file for complete search history.

(56) References Cited

FOREIGN PATENT DOCUMENTS

WO    2011/149778 A1    12/2011

OTHER PUBLICATIONS

Shangguan et al., "The Reaction of Thio Acids with Azides: A New Mechanism and New Synthetic Applications" JACS Communications (2003) vol. 125 pp. 7754-7755 (Year: 2003).*
Bin et al., "Total synthesis of the aminopropyl functionalized ganglioside GM1" Science China (2012) vol. 55 No. 1 pp. 31-35 (Year: 2012).*
Laura Morelli et al: "Synthesis of Neisseria Meningitis X Capsular Polysaccharide Fragments", ARKIVOC, vol. 2013, No. 2, Jan. 1, 2013, pp. 166-184.
F. Micoli et al: "Development of Glycoconjugate Vaccine to Prevent Meningitis iin Africa Caused by Meningococcal Serogroup X", Proceedings of the National Academy of Sciences, vol. 110, No. 47, Nov. 4, 2013, pp. 19077-19082.
Laura Morelli et al: "Synthesis and Immunological Evaluation of Protein Conjugates of Neisseria Meningitis X Capsular Polysaccharide Fragments", Beilstein Journal of Organic Chemistry, vol. 10, Oct. 13, 2014, pp. 2367-2376.

* cited by examiner

*Primary Examiner* — Eric Olson
(74) *Attorney, Agent, or Firm* — W&C IP

(57) ABSTRACT

The present invention relates to synthesis of novel higher oligomers and process of preparing the same. In particular the present invention relates to the chemical synthesis of oligomers of *Neisseria meningitidis* serogroup X ('hereinafter Men-X), more particularly tetramer. The present invention provides Men-X capsular oligomers obtained from synthetic pathway using purified saccharides of specific chain length and provides said novel oligomers as candidates for the development of conjugate vaccine against bacterial meningitis caused due to Men-X infections.

19 Claims, 10 Drawing Sheets

SYNTHETIC OLIGOMERS OF *NEISSERIA MENINGITIS* SEROGROUP X AND PROCESS OF PREPARING THEM

FIELD OF THE INVENTION

The present invention relates to synthesis of novel oligomers and process of preparing the same. In particular the present invention relates to the chemical synthesis of oligomers of *Neisseria meningitidis* serogroup X (hereinafter Men-X), more particularly tetramer and its use as a candidate for development of conjugate vaccine against bacterial meningitis caused due to Men-X infections.

BACKGROUND OF THE INVENTION

Bacterial meningitis causes approximately 1,70,000 annual deaths, with at least 5-10% case fatality in industrialized countries and a 20% case fatality in the developing world. *Streptococcus pneumoniae, Haemophilus influenzae* type b (Hib) and *Neisseria meningitidis* are responsible for most of the cases of bacterial meningitis worldwide.

In total 13 different serogroups namely A, B, C, D, 29E, H, I, K, L, W135, X, Y and Z of *N. meningitidis* have so far been identified, but about 90% of the infections are due to serogroups A, B, C, Y and W135. Whereas, serogroup X of *N. meningitidis* (Men-X) recently emerged as a substantial threat to public health. The occurrence of serogroup X was reported in North America, Europe, Australia, and West Africa.

Vaccination is considered to be the most effective way for controlling the spread of infectious diseases. There are several meningococcal vaccines which cover meningococcal serogroups A, C, Y and W, however, currently there is no licensed vaccine in the market which can protect from meningitis caused by serogroup X. So, there is a need to develop more comprehensive vaccines capable to offer broader protection covering serogroup X.

Currently conjugate vaccines are developed to offer higher protection against polysaccharide antigens which is created by covalently attaching a poor (polysaccharide) antigen to a carrier protein, preferably from the same microorganism), thereby conferring the immunological attributes of the carrier on the attached antigen through a T-cell dependent immune response.

Advances in the synthesis of oligosaccharides or polysaccharides, and new technologies developed in biological research have opened a new avenue in carbohydrate vaccine design. Numerous promising carbohydrate-based vaccine candidates have been prepared in recent years which include both naturally occurring carbohydrate and synthetically produced carbohydrate.

The naturally occurring carbohydrates prove to be an important component in the formation of vaccine but they have many drawbacks. The major drawbacks associated with naturally occurring carbohydrate are their isolation and purification which is itself very challenging. Further, any biological contaminants or process impurity which is left behind call for various quality assurance issues. Further, the inconsistency in polysaccharide quality and issues of polysaccharide size distribution lead to batch failures. The bacterial polysaccharides are required to be modified before it can be used for conjugation, leading to damage to the epitopes to varied extent.

While, the synthetic carbohydrate based vaccines have many advantages over the naturally occurring carbohydrates which includes, their well-defined chemical structure. Also there are less chances of any biological contamination and hence offer a better safety profile. Further, synthetic molecules can be modified during synthesis as per requirement to enhance the yield during conjugation and minimizing the damage to immunogenic epitopes during conjugation process by means of an in-built linker attached to the oligosaccharide molecule.

In view of the increasing incidences of the Men-X disease, several methods have been deployed for preparing synthetic Men-X oligosaccharide which can mimic the natural polysaccharide. For instance, the International patent application no. PCT/US2011/037364 titled "Synthetic oligosaccharide for *Neisseria meningitidis* vaccine" discloses a method for the chemical synthesis of oligosaccharide and conjugate thereof. The invention further provides immunogenic and immunoprotective compositions and antibodies thereof for diagnosing, treating and preventing infections caused by *N. meningitidis*. Also, a published literature titled "Synthesis of *Neisseria meningitidis* X capsular polysaccharide fragments" by Laura Morelli and Luigi Lay; Volume 2013, Issue 2, ARKIVOC discloses the synthesis of three conjugatable Men-X capsular polysaccharide fragments.

The existing systems presently in use for the oligosaccharide synthesis involve cumbersome production and purification procedures for synthesizing bacterial Men-X polysaccharides. The methods are either time consuming or give rise to a mixture of different sizes of oligomers. There is a general statement on preparation of successive oligosaccharides, but there is no enabling disclosure on the preparation of Men-X tetramer and further higher MenX oligomers. The above disclosed prior arts teach the chemical synthesis of the Men-X dimer and trimer capsular polysaccharide. They do not disclose the formation of tetramer and are not able to produce high yields of dimer and trimer.

The trimer conjugates reported in the Beilstein J. Org. Chem. 2014, 10, 2367-2376 are not able to provide good immunogenicity. Also the prior art uses −40° C. for O-thexyldimethylsilyl chloride (OTDS) deprotection in the initial steps of synthesis and require 8-9 days for the alpha-phosphorylation, whereas the present invention is carried out at 0° C. to room temperature and is completed in much lesser time. Further, prior art discloses hydrogenation reaction for 24-48 hours whereas present invention requires lesser time for the hydrogenation reaction.

OBJECT OF THE INVENTION

Thus the main object of present invention is the synthesis of novel Men-X capsular oligomers, preferably Men-X tetramer.

Another object of the present invention is to provide a process for the synthesis of novel Men-X capsular oligomers, preferably Men-X tetramer.

Yet another object of the present invention is to provide a synthetic pathway using purified saccharides of specific chain length.

Yet another object of the present invention is to provide synthetic Men-X capsular oligomers capable of being used in conjugate vaccines against *N. meningitidis* with enhanced efficacy.

Yet another object of the present invention is to provide a process for the preparation of synthetic Men-X capsular oligomers which meet the physico-chemical quality standards for the purity.

Yet another object of the invention is its cost effectiveness, increased efficacy and improved shelf-life.

SUMMARY OF THE INVENTION

Accordingly, the present invention relates to the synthesis of novel Men-X capsular oligomers and process of synthesizing said Men-X capsular oligomers by combining of two building blocks for the construction of Men-X oligosaccharide backbone. The two building blocks are named propagation unit and termination unit. The propagation unit is added to the terminal unit which terminates the chain at either end.

The starting material used for the synthesis of propagation unit is sugar monosaccharide including Glucosamine hydrochloride, which is an abundant and cheap starting material.

In one embodiment, the crucial step in this synthesis is preparation of alpha or beta anomer, preferably an alpha anomer of sugar phosphonate.

The whole synthetic sequence is optimized on multigram scale in such a way that it includes column purification only in few steps. The glycosidation result in to the formation of alpha-anomer along with beta-anomer attached with linker moiety. The anomeric mixture is deprotected and separated using column chromatography resulted in to production of terminal group with alpha or beta linker stereochemistry. The said purified form is confirmed by $^1$H-NMR analysis.

The dimer is prepared by combining propagation unit and terminal unit by using coupling reagent like pivaloyl chloride followed by oxidation using Iodine. In order to prepare trimer from dimer, the protecting group e.g. acetate group of dimer is deprotected and coupled with propagation unit using similar conditions for the generation of dimer.

The iterative acetate deprotection and coupling would provide tetramer unit. The final steps include one step conversion of azide groups to NHAc if required followed by removal of protective groups like acetate, benzyl and Cbz deprotection by base treatment and hydrogenation would provide the desired Men-X higher oligomers including tetramer, pentamer, hexamer etc (comprising linker).

The present invention results in synthesizing the novel higher oligomers in very short duration of time.

The present invention enables the attachment of 6C linker with the oligomers which results in minimizing the steric hindrance by providing flexibility during conjugation.

Also, the 6C linker in the present invention is attached directly with the sugar ring instead of attachment through phosphate in case of prior art. This positioning of linker is suitably optimized resulting in enhancement of immunogenicity as well as the yield of conjugate vaccine and will give better stability to the compound.

All the illustrative steps devised for the synthesis of Men-X capsular polysaccharide using novel approach results in better yield of oligomers, enhanced antigenicity as shown in FIG. 1 and purity of more than 95% as shown in FIG. 7 and FIG. 10.

DETAILED DESCRIPTION OF THE INVENTION

Figure 1:
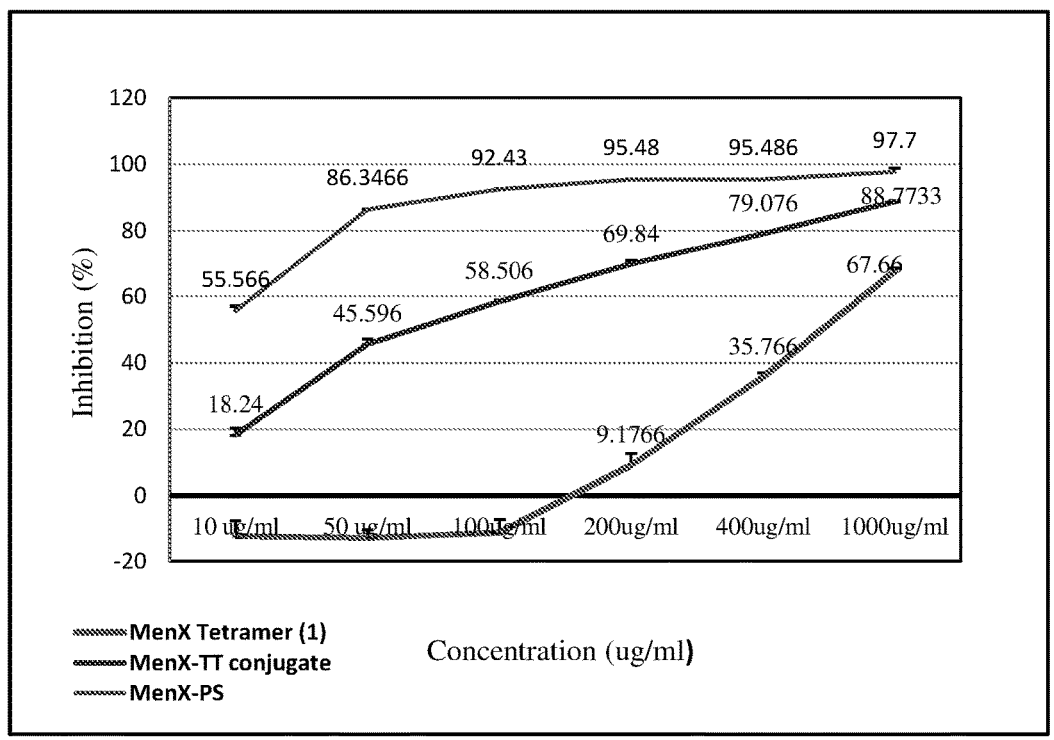
FIG. 1 depicts graphical representation of percentage inhibition of binding of anti-Men-X antibodies to bacterial polysaccharide in an Inhibition ELISA with bacterial polysaccharide, synthetic Men-X Tetramer with alpha linker (1) and synthetic Men-X Tetramer-TT conjugates with alpha (1-TT) linker.
Figure 2:
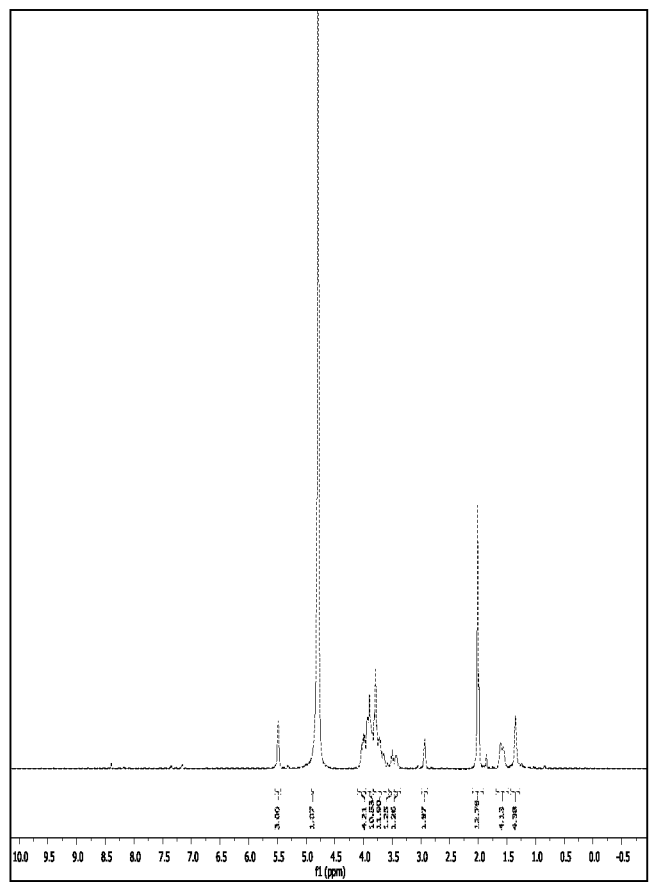
FIG. 2 depicts $^1$HMR spectrum of Men X tetramer having α-linker (1)
Figure 3:
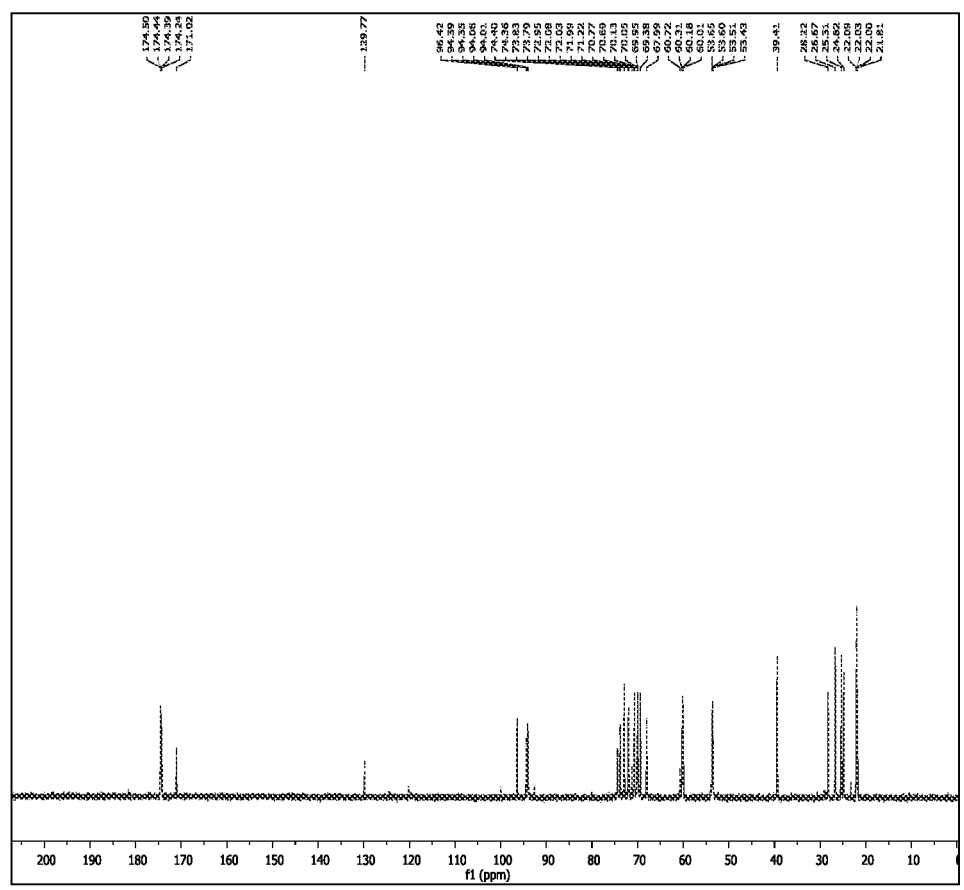
FIG. 3 depicts $^{13}$C NMR spectrum of 1
Figure 4:
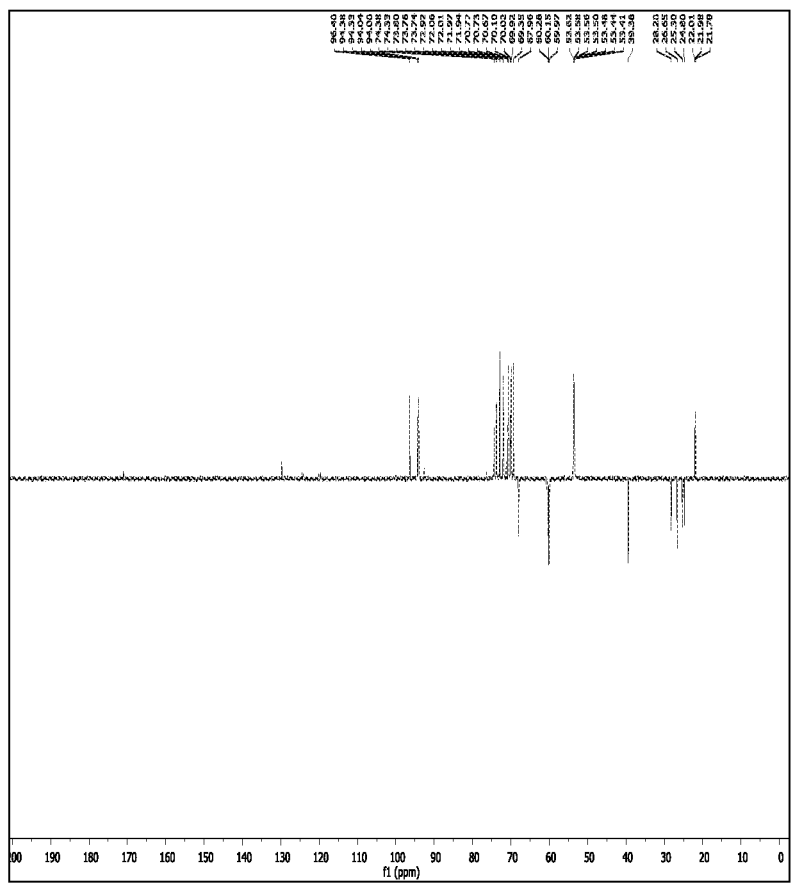
FIG. 4 depicts DEPT-NMR spectrum of 1
Figure 5:
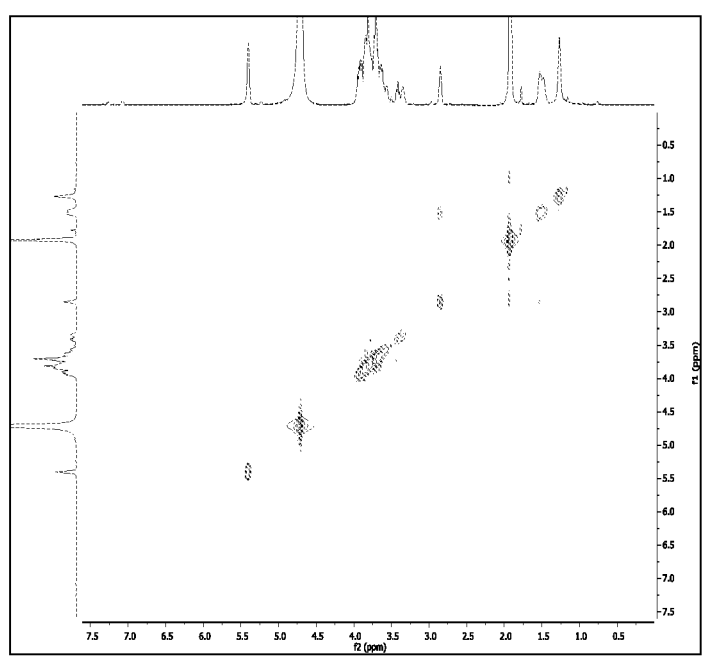
FIG. 5 depicts 2D COSY NMR spectrum of 1
Figure 6:
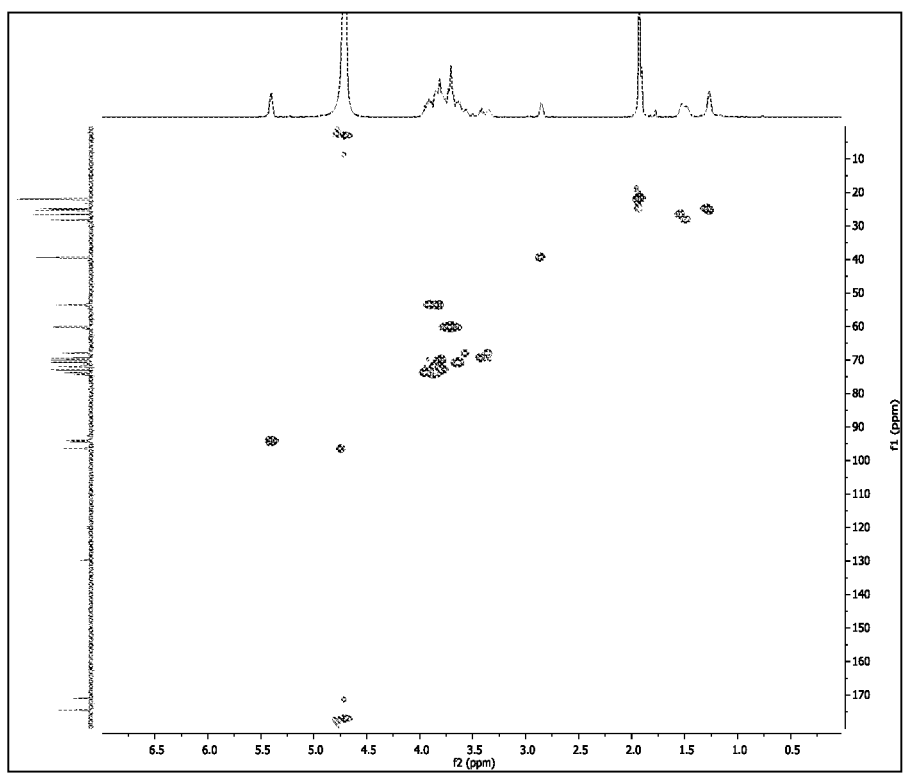
FIG. 6 depicts 2D HSQC NMR spectrum of 1
Figure 7:
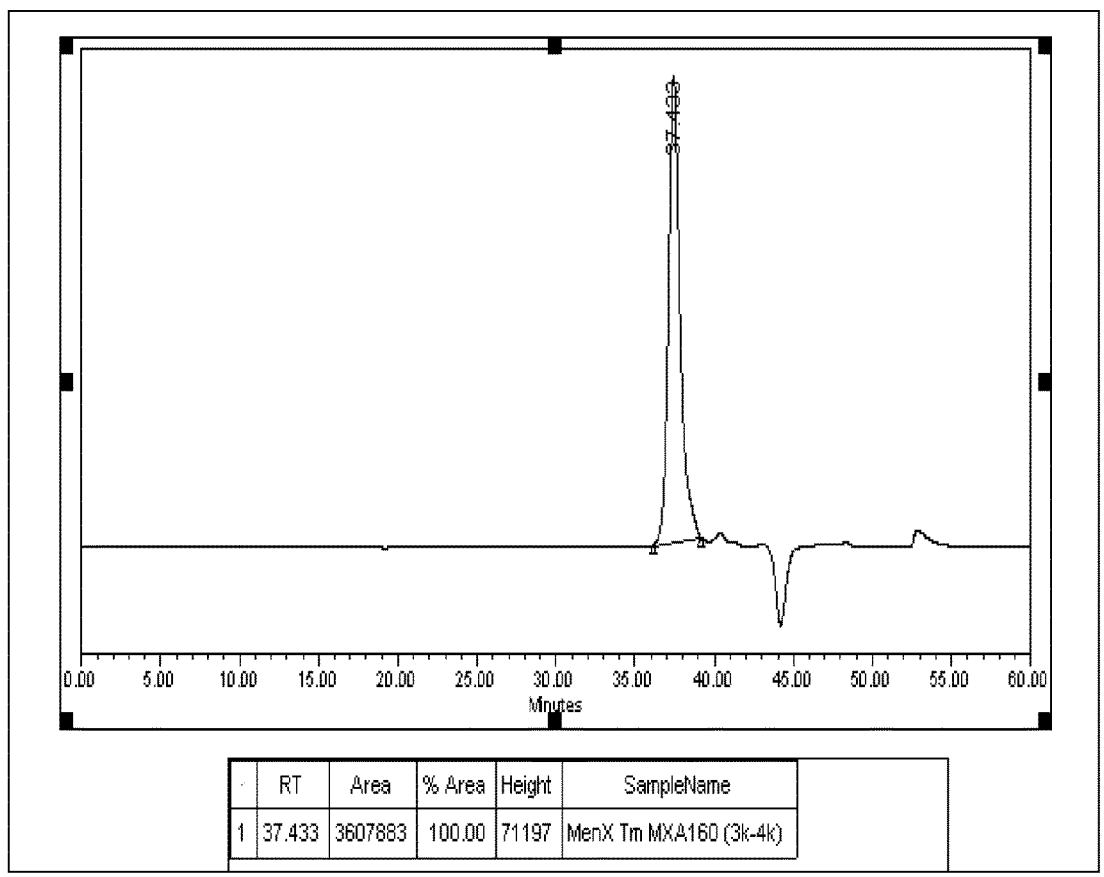
FIG. 7 depicts HPLC chromatogram of 1
Figure 8:
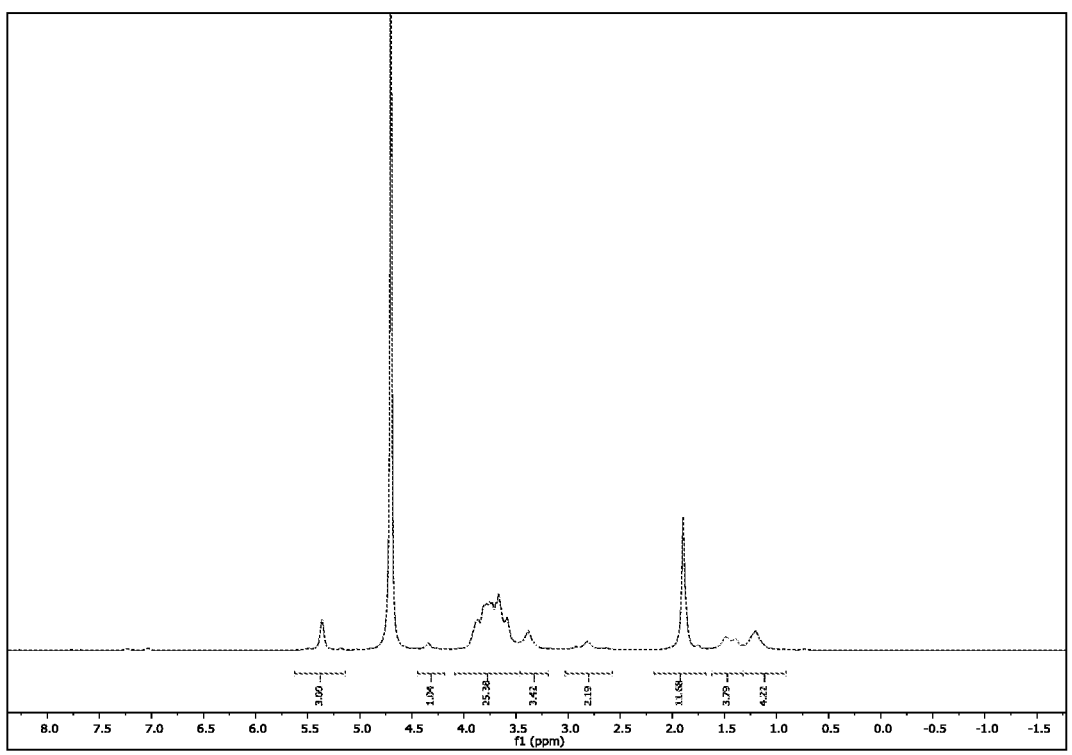
FIG. 8 depicts $^1$HMR spectrum of Men X tetramer having β-linker (1A)
Figure 9:
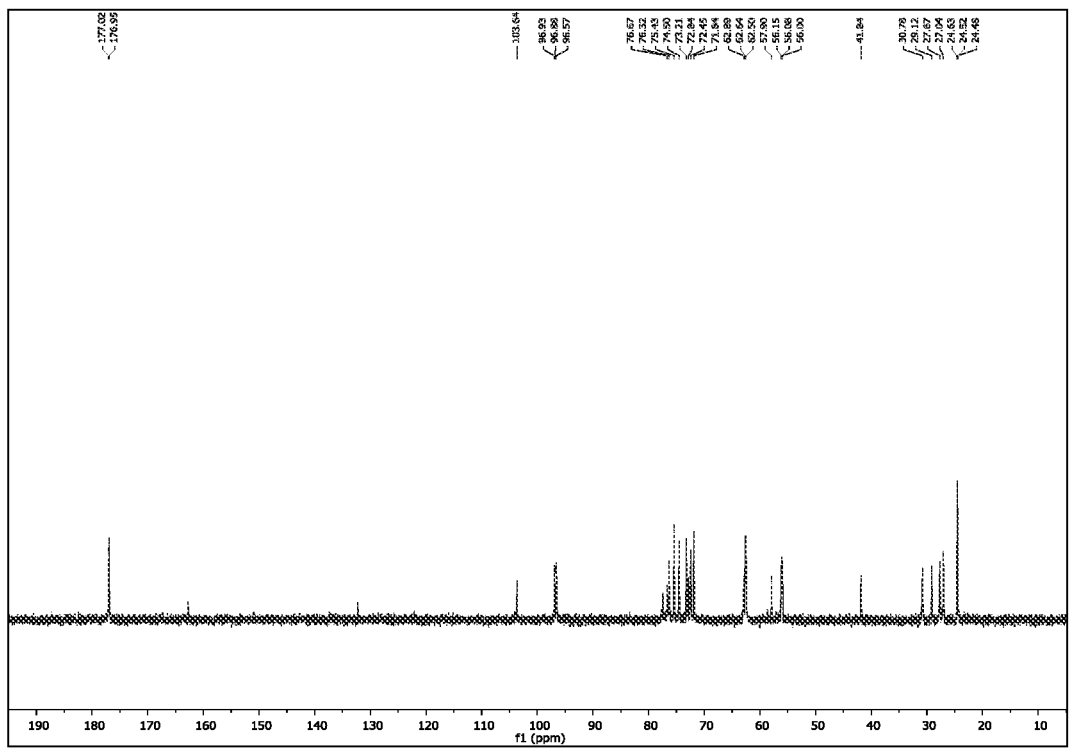
FIG. 9 depicts $^{13}$C NMR spectrum of α-linker (1A)
Figure 10:
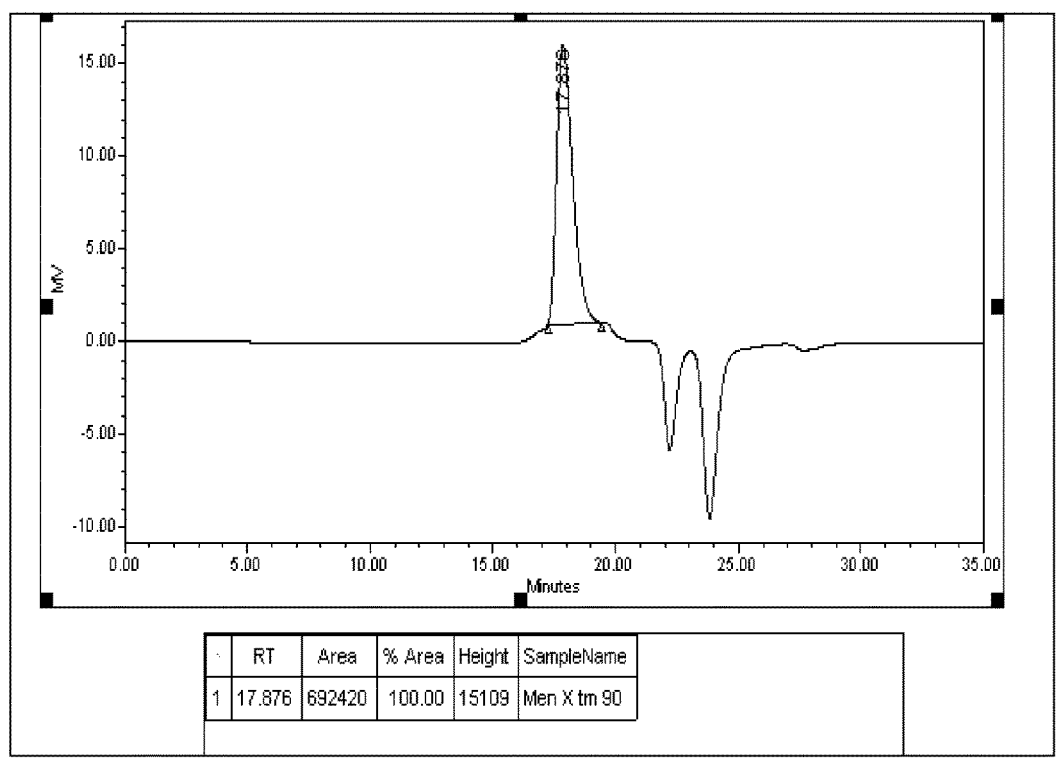
FIG. 10 depicts HPLC chromatogram of 1A

Accordingly, the present invention relates to the chemical synthesis of the meningitis capsular oligosaccharide more particularly Men-X oligosaccharide for the development of conjugate vaccine against *Neisseria meningitidis*, often referred to as meningococcus, which is one of the causative agents for bacterial meningitis and other forms of meningococcal disease such as meningococcemia. The said synthesis being accomplished in the following steps:

1. Synthesis of Hemiacetal (compound 10) as shown in Scheme 1.
2. Synthesis of Propagation Unit (compound 12) and Terminal unit (compound 14) as shown in scheme 2.
3. Synthesis of higher oligomers as shown in Scheme 3.

Before the preferred embodiment of the present invention is described, it is understood that this invention is not limited to the particular materials described, as they may vary. It is also understood that the terminology used herein is for the purpose of describing the particular embodiment only, and is not intended to limit the scope of the invention in any way.

It must be noted that as used herein, the singular forms "a", "an" and "the" include plural reference unless the context clearly dictates otherwise.

The terminology 'compound' and 'compd' has been used interchangeably.

Synthesis of Hemiacetal Unit:

In one of the embodiment of the invention, Scheme 1 depicts the synthesis of hemiacetal (10). The starting material used in the synthesis of Men-X capsular oligosaccharide is a sugar selected from glucosamine HCl, more specifically but not limited to D(±) Glucosamine HCl compound (compound 2).

Scheme 1. Synthesis of Hemiacetal unit (compound 10)
4-O-acetyl-2-azido-3, 6-di-O-benzyl-2-deoxy-α,β-D-glucopyranose

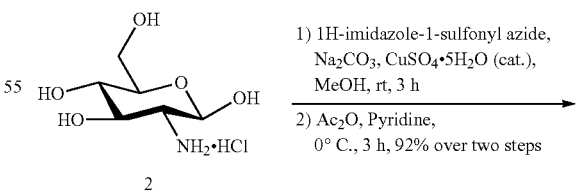

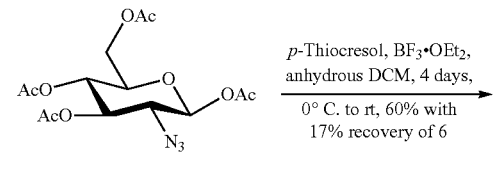

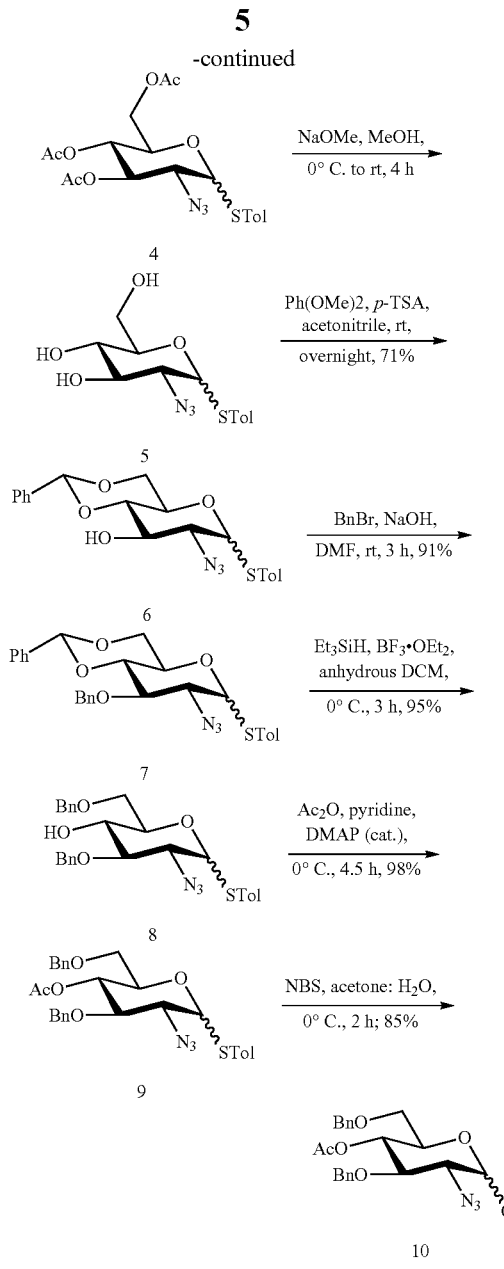

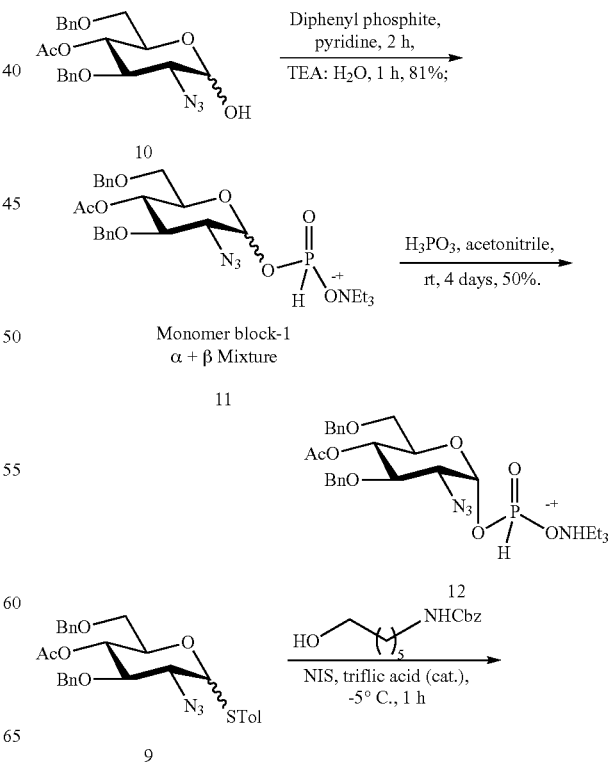

[PhCH(OMe)$_2$], p-Toluenesulfonic acid (p-TSA), acetonitrile overnight at room temperature in presence or absence of organic solvent selected from but not limited to acetonitrile or dichloromethane. The reaction results in formation of compound 6 which is then subjected to benzyl protection with Benzyl Bromide and Sodium Hydroxide in presence of organic solvent selected from is selected from but not limited to dimethyl formamide (DMF) and dimethyl sulphoxide for 2 to 4 hours preferably 3 hours at room temperature. The above reaction result in formation of compound 7. The compound 7 is then subjected to regioselective ring opening while reacting with Triethyl Silane (Et$_3$SiH) and Boron trifluoride diethyl etherate (BF$_3$.OEt$_2$) in solvent selected from but not limited to anhydrous dichloromethane (DCM), chloroform, tetrahydrofuran at 0° C. for 2 to 4 hrs, preferably 3 hrs resulting in compound 8. The compound 8 undergo acetylation while reacting with Acetic Anhydride (Ac$_2$O) in presence of solvent selected from but not limited to pyridine and dichloromethane and 4-Dimethylaminopyridine (DMAP) (cat.) at 0° C. for 3.5 to 5 hours, preferably 4.5 hrs resulting in compound 9. The compound 9 so obtained is subjected to Thio-tolyl deprotection while reacting with N-Bromosuccinimide (NBS) in equimolar ratio selected from but not limited to acetone: H$_2$O, dicholoromethane: H$_2$O at 0° C. for 1 to 3 hours, preferably 2 hr to obtain compound 10.

The said compound 10 serve as the common intermediate to synthesize the propagation unit (12) as well as two terminal unit(s) namely 14 and 14A.

The schematic representation of preparation of propagation and terminal units are shown as below in Scheme 2.

Scheme 2: Synthesis of Propagation unit (compound 12) and Terminal unit(s) (compound 14 and compound 14A).

The glucosamine HCl is subjected to diazotransfer reagent such as but not limited to imidazole-1-sulfonyl azide, Na$_2$CO$_3$, CuSO$_4$.5H$_2$O in presence of pyridine to obtain compound 3. The organic solvent used to convert compound 2 to compound 3 is selected but limited to methanol or ethanol, or a combination of either with water. The compound 3 so obtained is reacted with donor group such as p-thiocresol, Boron trifluoride diethyl etherate (BF$_3$.OEt$_2$) and anhydrous Dichloromethane (DCM) for 3 to 4 days at 0° C. to room temperature resulting in compound 4. The organic solvent used to convert compound 3 to compound 4 is selected from dichloromethane, acetonitrile or chloroform. The compound 4 so obtained is subjected to deacetylating reagent such as Sodium methoxide in presence of organic solvent selected from combination of methanol or ethanol or their mixture in water for 3 to 7 hours, preferably 4 hours at 0° C. to room temperature resulting in compound 5. The compound 5 so obtained is undergone benzylidene protection by reacting it with Benzaldehyde dimethyl acetal -continued

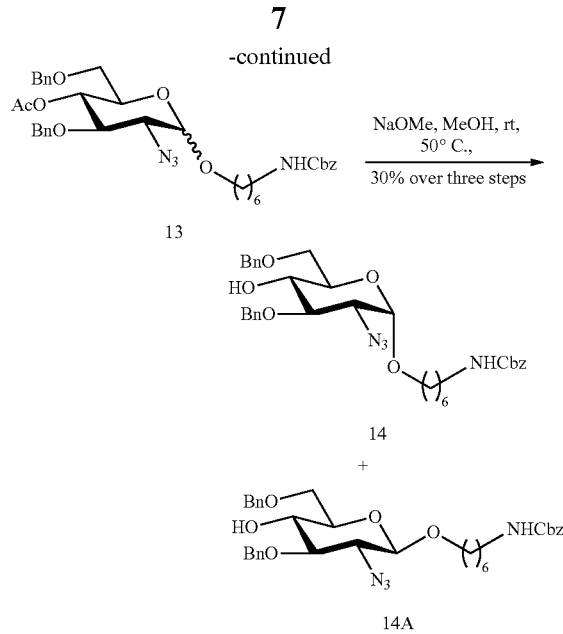

The Compound 10 so obtained from the Scheme 1 is subjected to phosphitylation agent not limited to Di-phenyl phosphite pyridine and then equally molar mixture of triethylamine ($Et_3N$-TEA) and $H_2O$ (1:1) for 2 hour preferably 1 hour at room temperature (85%) for substitution of terminal hydrogen to get Compound 11 which is the monomeric block containing both alpha and beta mixtures. The Compound 11 so obtained is reacted with phosphoric acid ($H_3PO_4$) and acetonitrile at room temperature for 4 days for the selective and absolute receiving of alpha anomer of compound 11 as compound 12. The compound 12 so obtained act as a Propagation Unit in the synthesis of Men-X tetramer.

The compound 9 is treated with linker 6-(Z-Amino)-1-hexanol in presence of N-iodo succinimide (NIS) and triflic acid in tetrahydrofuran at −5° C. for 1 hour resulting in compound 13. The compound 13 is subjected to deacetylation by reacting with NaOMe, MeOH at room temperature to 50° C., in consecutive three steps to obtain termination unit (s). Termination unit(s) so obtained are subject to separation by silica gel column chromatography resulting in obtainment of compound 14 ($R^1$=—($CH_2)_6$NHCbz, $R^2$=H) with 6C linker oriented in alpha position and compound 14A ($R^1$=H, $R^2$=—($CH_2)_6$NHCbz) with 6C linker oriented in beta position.

The compounds 14 and 14A so obtained act as termination unit(s) for the synthesis of oligomers.

Oligomer Synthesis:

Once the propagation unit and terminal unit(s) are prepared the subsequent oligomers can be prepared thereafter by below mentioned processes and as shown in scheme 3.

The dimer is prepared by reacting propagation unit 12 with terminal unit 14 to yield compound 15 (alpha anomer with $R^1$=—($CH_2)_6$NHCbz, $R^2$=H, $R^3$=Ac). Similarly the propagation unit 12 is reacted with terminal unit 14A to yield dimer compound 15A (beta anomer with $R^1$=H, $R^2$=—($CH_2)_6$NHCbz, $R^3$=Ac). The above reactions of preparing the dimer are carried out in the presence of coupling reagent not limited to pivaloyl chloride coupling reagent in pyridine at room temperature for 30 minutes followed by oxidation using Iodine at −40° C., in pyridine: $H_2O$ (9.75:0.25) for 1.5 hours (86%) resulting in dimer compound 15 and compound 15A (69%) with good yield.

Scheme 3. Synthesis of Higher Oligomers (dimer, trimer and tetramer)

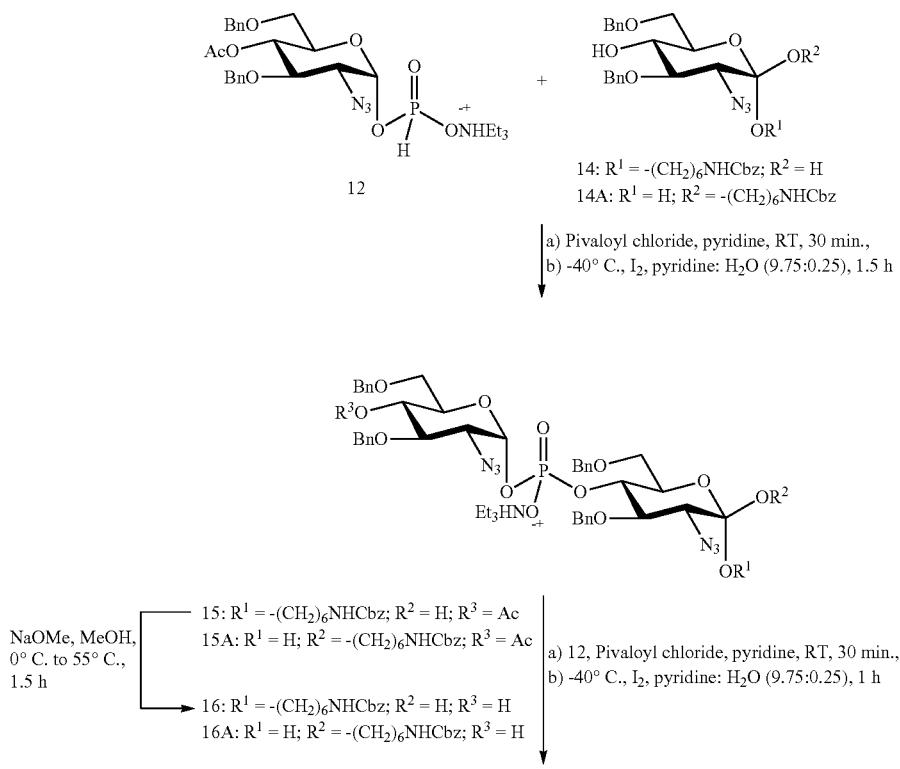

-continued

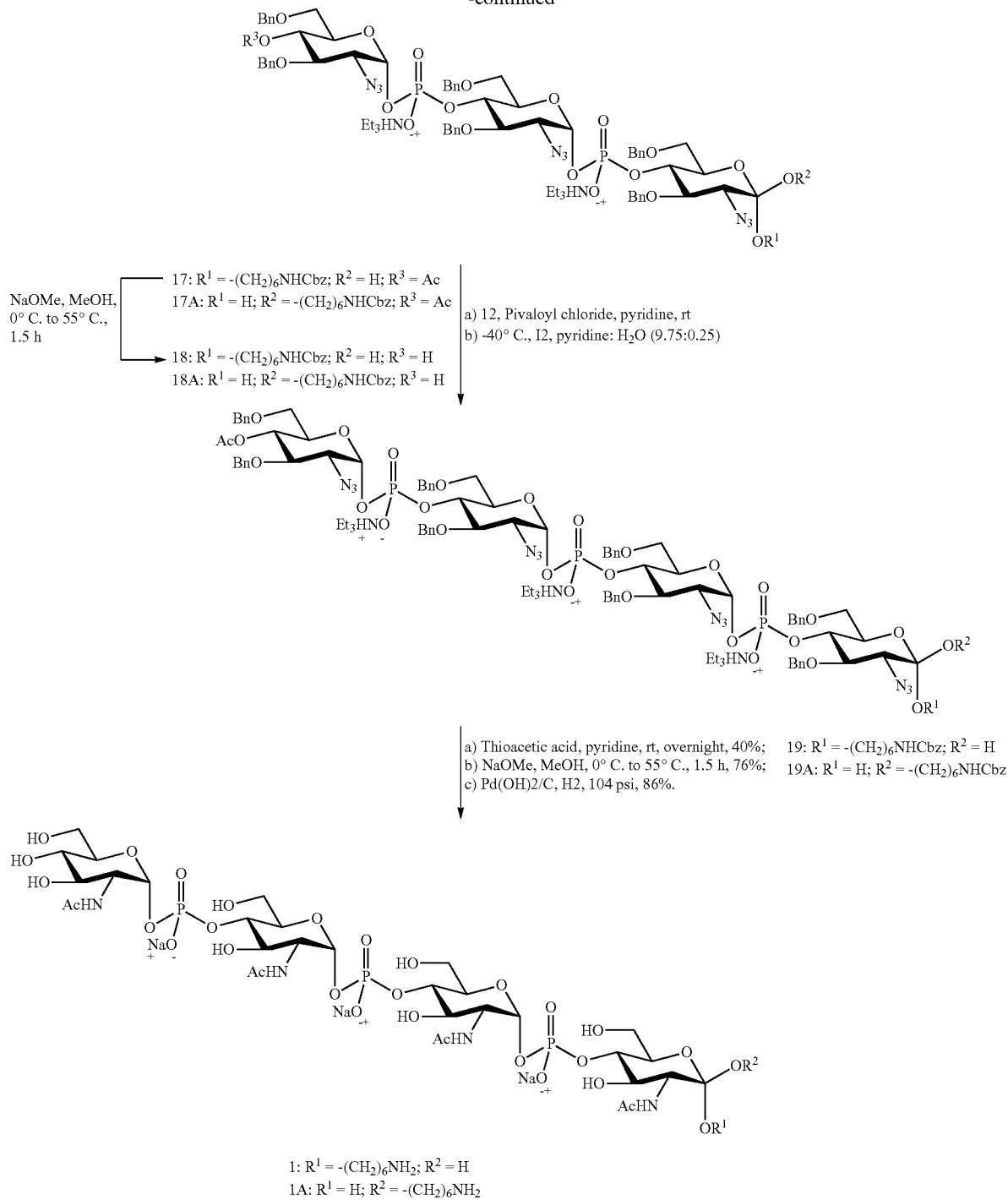

The dimer compound 15 and compound 15A so obtained is deacetylated by reacting with base such as Sodium methoxide in methanol at 0° C. to 55° C. for 1.5 hrs to obtain compound 16 (Quantitative) (alpha anomer with $R^1$=—$(CH_2)_6NHCbz$, $R^2$=H, $R^3$=H) and compound 16A (78%) (beta anomer with $R^1$=H, $R^2$=—$(CH_2)_6NHCbz$, $R^3$=H) respectively.

Thereafter, dimeric compounds (compound 16 and compound 16 A) so obtained are again coupled with the propagation unit 12 using similar coupling reagents and conditions for generation of trimer compound 17 (alpha anomer with $R^1$=—$(CH_2)_6NHCbz$, $R^2$=H, $R^3$=Ac) and compound 17 A (beta anomer with $R^1$=H, $R^2$=—$(CH_2)_6NHCbz$, $R^3$=Ac) respectively with high yield.

The resultant compound 17 and compound 17 A are independently subjected to deacylating reagents resulting in compound 18 (alpha anomer with $R^1$=—$(CH_2)_6NHCbz$, $R^2$=H, $R^3$=H) and compound 18 A (beta anomer with $R^1$=H, $R^2$=—$(CH_2)_6NHCbz$, $R^3$=H) respectively.

The resultant compounds 18 and 18 A so obtained are subject to iterative reactions conditions to obtain higher synthetic oligomers (X and XA) including tetramers (1 and 1A), pentamers, hexamers etc, more preferably tetramer of compound 19 (alpha anomer with $R^1$=—$(CH_2)_6NHCbz$, $R^2$=H) and compound 19 A (beta anomer with $R^1$=H, $R^2$=—$(CH_2)_6NHCbz$).

The compounds 19 and 19 A so obtained are subject to treatment with (a) thioacetic acid and pyridine at room temperature resulting in the conversion of azide groups to NHAc followed by (b) aceatate group deprotection and (c) benzyl and Cbz deprotection by hydrogenation which results in higher synthetic oligomers (X and XA) including tetramers (1 and 1A), pentamers, hexamers etc.

Both the anomeric epimers of Men-X oligomers can be deduced by following the above mentioned schemes.

The tetramers (1) and (1A) so obtained are rapidly synthesized within a short duration of time. The time taken to synthesize said tetramers (1) and (1A) is in the range of 225 hours to 276 hours, preferably in 257 hours.

Anyone or both the anomeric oligomers so obtained i.e. Men-X tetramer 1 and Men-X tetramer 1A are used as a potential candidate for development of conjugate vaccine against bacterial meningitis caused due to Men-X infections.

Men X Tetramer 1

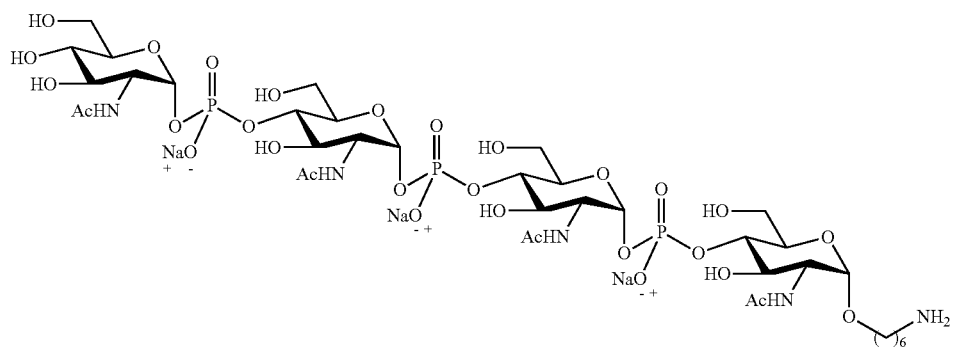

Men X Tetramer 1A

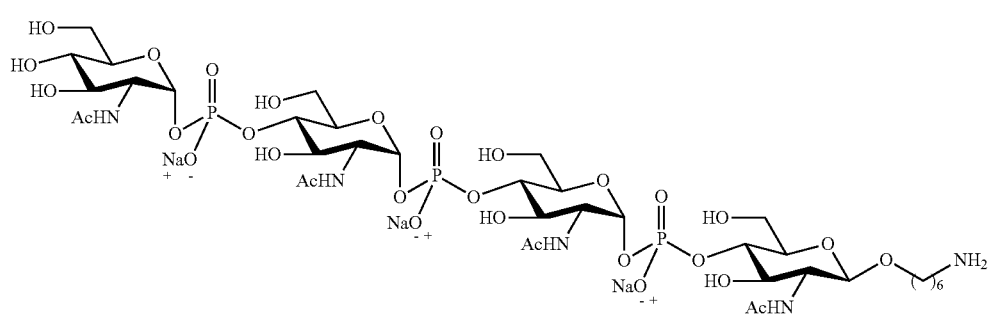

The above detailed description of process is illustrated by non-limiting examples:

EXAMPLES

Example 1: Synthesis of Compound 3

1,3,4,6-Tetra-O-acetyl-2-azido-2-deoxy-D-glucopyranose (3)

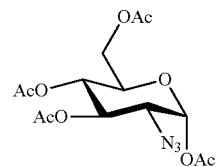

To the stirred solution of glucosamine (20 gm, 93 mmol) in methanol was added 1H-imidazole-1-sulfonyl azide (19.3 gm, 110 mmol) followed by addition of anhydrous sodium carbonate (19.7 gm, 186 mmol). The reaction mixture was left to stir at room temperature (rt) under nitrogen atmosphere for 15 min. To the reaction mixture $CuSO_4.5H_2O$ (97 mg, 9.3 mmol) was added and stirred at rt for 3 h. After completion of reaction (monitored by TLC), the reaction mixture was filtered through Buchner funnel. The solid residue washed with 10% methanol:ethyl acetate (200 mL). The crude reaction mass 2-azido-2-deoxy-D-glucose (20 g) was used as such in the next step.

To the stirred solution of 2-azido-2-deoxy-D-glucose (20 gm, 97 mmol) in pyridine (120 mL) was added acetic anhydride (80 mL, 776 mmol) dropwise. Reaction mixture left to stir at 0° C. for 1 h and at rt for 2 h. After completion of reaction, (monitored by TLC), the reaction mixture was concentrated under reduced pressure (to remove excess pyridine). The solid residue was diluted with $H_2O$ (200 mL) and extracted with 30% ethyl acetate:pet ether (200 mL) for two times. The organic layers were dried over anhydrous sodium sulfate, filtered and concentrated. 16 g of pure product 3 obtained with 92% yield for two steps.

Example 2: Synthesis of Compound 4

4-Methylphenyl 3,4,6-tri-O-acetyl-2-azido-2-deoxy-1-thio-α,β-D-glucopyranoside (4)

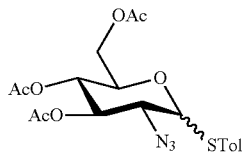

To the stirred the solution of 1,3,4,6-Tetra-O-acetyl-2-azido-2-deoxy-D-glucopyranose (3) (120 gm, 321 mmol) in DCM (1.2 lit) was added p-thiocresol (79.8 gm, 643 mmol) at 0° C. under nitrogen atmosphere. The reaction mixture was stirred for 5 min followed by dropwise addition of $BF_3.OEt_2$ (119 mL, 965 mmol) over 30 min. under nitrogen atmosphere. The reaction left to stir at rt for 72 h. After consumption of maximum starting material (monitored by TLC), the reaction mixture was cooled to 0° C. and diluted with $NaHCO_3$ (1 L) till pH neutralization. The extracted organic layers dried over anhydrous sodium sulphate, filtered and concentrated under reduced pressure. The crude reside was purified by flash gel column chromatography using 2% ethyl acetate:pet ether as an eluent to afford yellow syrup compound 4, 80 gm, 60% yield.

Example 3: Synthesis of Compound 5

4-Methylphenyl 2-azido-2-deoxy-1-thio-α,β-D-glucopyranoside (5)

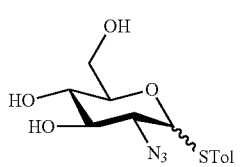

To the stirred solution of per-acetylated thioglycoside 4 (82 gm, 187 mmol) in MeOH (1 Lit.) was added NaOMe (40.4 gm, 437 mmol) portion-wise over 30 min. at 0° C. under nitrogen atmosphere. The reaction mixture was left to stir at rt for additional 3 h. After completion of reaction (monitored by TLC), acetic acid was added to the reaction mixture till the pH of reaction mixture becomes neutral. The reaction mixture was extracted with ethyl acetate (800 mL) for two times. The separated organic layers were dried over anhydrous sodium sulphate, filtered and concentrated under reduced pressure. 110 g of crude product used directly in the next step.

Example 4: Synthesis of Compound 6

4-Methylphenyl 2-azido-4,6-O-benzylidene-2-deoxy-1-thio-α,β-D-glucopyranoside (6)

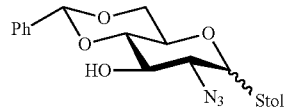

To the stirred solution of triol thioglycoside 5 (110 gm, 353 mmol) in acetonitrile (1 L) was added benzaldehyde dimethyl acetal (106 mL, 707 mmol) followed by addition of PTSA (6.6 gm, 35.3 mmol) in one portion. The reaction mixture was left to stir at rt for overnight. After completion of reaction (monitored by TLC), the reaction mixture was diluted with water (1 L) and extracted with ethyl acetate (1 L) for two times. The combined organic layers were dried over anhydrous sodium sulphate, filtered and concentrated under reduced pressure. The crude mass was diluted with DCM (500 mL) followed by addition pet ether (2 L) resulted in to product precipitation (white off solid). The precipitate filtered over Buchner funnel, the buff white residue collected and dried. 100 gm, 71% of the pure product 6 isolated.

Example 5: Synthesis of Compound 7

4-Methylphenyl 2-azido-4,6-O-benzylidene-3-O-benzyl-2-deoxy-1-thio-α,β-D-glucopyranoside (7)

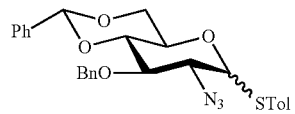

To the stirred solution of benzylidene alcohol 6 (90 gm, 225 mmol) in DMF (300 mL) was added NaOH (22 gm, 563 mmol) followed by 20 addition of catalytic amount of TBAI (4.1 gm, 11.25 mmol) at rt under nitrogen atmosphere. The reaction mixture was left to stir at rt for 15 min. followed by dropwise addition of benzyl bromide (52.2 mL, 450 mmol) over 30 min. The reaction mixture was stirred at rt for additional 3 h. After completion of reaction (monitored by TLC), the reaction mixture was diluted with ice cold water (900 mL) which resulted into solid precipitation. The solid mass filtered off through the Whatman filter paper. The solid mass was washed with water (500 mL) followed by pet ether (450 mL) for two times, the residue was dried over vacuum. 100 g of the buff white solid obtained as a pure product 7 in 91% yield.

Example 6: Synthesis of Compound 8

4-Methylphenyl 2-azido-3,6-di-O-benzyl-2-deoxy-1-thio-α,β-D-glucopyranoside (8)

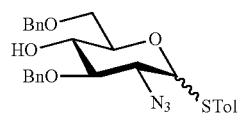

To the stirred solution of compound 7 (30 gm, 61.27 mmol) in DCM (600 mL) was added triethyl silane (117 mL, 735 mmol) at 0° C. under nitrogen atmosphere. The reaction mixture was left to stir at 0° C. for 15 min followed by dropwise addition of BF$_3$.OEt$_2$ (11.6 mL, 91.9 mmol) left to stir for 3 h at same temperature. After completion of reaction, the reaction mixture was diluted with saturated solution of sodium bicarbonate (300 mL) at 0° C. and the organic layer was separated by extraction. The aqueous layer extracted one more time with DCM (300 mL) and separated. The collected organics were dried over anhydrous sodium sulphate, filtered and concentrated under reduced pressure. The crude residue was purified by flash silica gel column chromatography using pet ether:ethyl acetate (7:3) as an eluent to afford white solid compound 8, 28 g. 95% yield.

Example 7: Synthesis of Compound 9

4-Methylphenyl 4-O-acetyl-2-azido-3,6-di-O-benzyl-2-deoxy-1-thio-α,β-D-glucopyranoside (9)

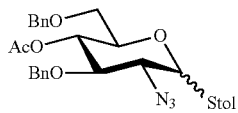

To the stirred solution of di-benzyl alcohol 8 (90 gm, 183 mmol) in pyridine (1 L) was added acetic anhydride (34.5 mL, 366 mmol) followed by DMAP (cat.) at 0° C. under nitrogen atmosphere. The reaction mixture was left to stir at rt for additional 3 h. After completion of reaction (monitored by TLC), the reaction mixture was concentrated under reduced pressure (to remove the excess pyridine). The residue was diluted with water (900 mL) and extracted with ethyl acetate (900 mL) for 2 times. The combined organics were dried over anhydrous sodium sulfate, filtered and concentrated. 85 g (98% yield) of pure product 9 obtained without purification.

Example 8: Synthesis of Compound 10

4-O-acetyl-2-azido-3,6-di-O-benzyl-2-deoxy-α,β-D-glucopyranose (10)

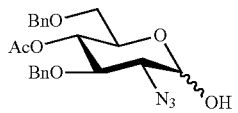

To the stirred solution of compound 9 (10 gm, 18.7 mmol) in acetone:water (7:1) (240 mL) was added NBS (13.3 gm, 74.9 mmol) portion-wise at 0° C. The reaction mixture was stirred at the same temperature for 30 min to 1 h. After completion of reaction (monitored by TLC), the reaction mixture was quenched with sat. sodium thiosulphate (20 mL) and concentrated under reduced pressure. The reaction mass was extracted with DCM (300 mL) for 3 times. The combined organics were dried over anhydrous sodium sulfate, filtered and concentrated. The crude mass was purified over silica using 10% ethyl acetate in pet ether to afford hydroxy compound 7 g, 85% yield as a buff white solid.

Example 9: Synthesis of Compound 12

4-O-Acetyl-2-azido-3,6-di-O-benzyl-2-deoxy-α-D-glucopyranosyl hydrogenphosphonate (12)

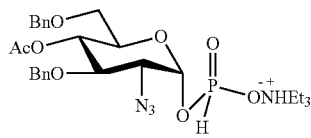

The hemiacetal compound 10 (4.5 g, 10.5 mmol) was dissolved in pyridine (45 mL) and treated slowly with diphenyl phosphite (14.1 mL, 73.7 mmol). The resulting reaction mixture was allowed to stir at room temperature for 2 h. The reaction mixture was diluted with Et$_3$N: H$_2$O (1:1, 40 mL) at 0° C. and left to stir further for 30 min. The reaction mixture was concentrated under reduced pressure and then was coevaporated using toluene for two times. The residue was diluted with sat. Na$_2$CO$_3$ (50 mL) and was extracted using DCM (60*2). The organic layers were filtered, dried over anhydrous sodium sulphate and concentrated under reduced pressure. The residue was purified by flash gel column chromatography using MeOH:DCM+1% TEA (05:95) as an eluent to afford pale yellow syrup phosphonate (4 g, 81%). The above obtained product of anomeric mixture of phosphonate (4 g, 6.6 mmol) and catalytic amount of phosphonic acid in anhydrous acetonitrile was stirred for 4 days at room temperature. Reaction quenched by adding triethylamine (2.5 mL) at 0° C., concentrated under vacuum and diluted with sat. Na$_2$CO$_3$ (100 mL) and extracted in DCM (100 mL*2). The organic layers were dried (Na$_2$SO$_4$) and concentrated under reduced pressure to give the crude product which was purified on flash silica using MeOH-DCM+1% Et$_3$N (3:97) as eluent to give pure compound 12 (2 g, 50%) as a brown dense syrup.

Example 10: Synthesis of Compound 14 and 14A 6-(Benzyloxycarbonyl)aminohexyl 2-azido-3,6-di-O-benzyl-2-deoxy-α-D-glucopyranoside (14) and 6-(Benzyloxycarbonyl)aminohexyl 2-azido-3,6-di-O-benzyl-2-deoxy-β-D-glucopyranoside (14A)

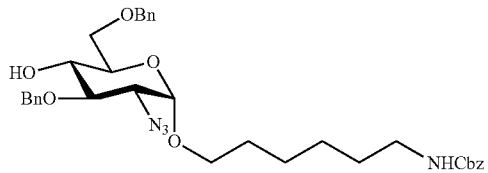

The mixture of 4-methylphenyl 4-O-acetyl-2-azido-3,6-di-O-benzyl-2-deoxy-1-thio-α,β-D-glucopyranoside (9) (6.8 g, 12.7 mmol), NIS (5.72 gm, 25.4 mmol) and benzyl N-(6-hydroxyhexyl)carbamate (3.8 gm, 15.2 mmol) was dissolved in THF (80 mL), stirred and cooled at −5° C. under inert atmosphere. To the above mixture triflic acid (0.05 mL) was added dropwise over 5 min and the reaction mixture was stirred at the same temperature for 1 h. After completion, the reaction mixture was diluted with saturated solution of Na$_2$S$_2$O$_3$ and NaHCO$_3$ (200 ml each). The reaction mixture was extracted with ethyl acetate (100 mL) for three times. The combined organic layers were dried over anhydrous sodium sulphate, filtered and concentrated under reduced pressure. The crude reaction mass carried forward for the deacetylation. The crude reaction mass was dissolved in methanol (70 mL) and was added NaOMe (2.2 gm) portion wise over 10 min at rt. The reaction mixture was heated at 50° C. for 1 h. After completion, the reaction mixture was cooled to room temperature and was neutralized with Amberlite IR 120 acidic resin till neutral pH. The reaction mixture was filtered through the Whatman filter paper and the filtrate was concentrated under reduced pressure. The crude product was purified by flash gel column chromatography using 15-20% ethyl acetate:pet ether as an eluent to afford the compound 14 (2.1 g, 27%) and 14A (1.8 g, 18% yield) as yellow thick syrup.

Example 11: Synthesis of Compound 15 and 15A 6-(Carbobenzyloxy)aminohexyl (4-O-acetyl-2-azido-3,6-di-O-benzyl-2-deoxy-α-D-glucopyranosyl phosphate)-(1→4)-2-azido-3,6-di-O-benzyl-2-deoxy-α-D-glucopyranoside, triethylammonium salt (15) and 6-(Carbobenzyloxy)aminohexyl (4-O-acetyl-2-azido-3,6-di-O-benzyl-2-deoxy-α-D-glucopyranosyl phosphate)-(1→4)-2-azido-3,6-di-O-benzyl-2-deoxy-β-D-glucopyranoside, triethylammonium salt (15A)

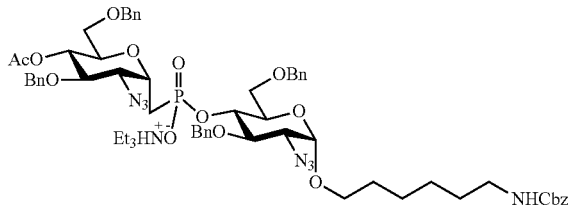

The mixture of α-H-phosphonate 12 (2.87 gm, 4.84 mmol) and alcohol 14 (1.5 gm, 2.42 mmol) was coevaporated with anhydrous pyridine under vacuum for three times. The mixture was dissolved in anhydrous pyridine (50 mL) and was added pivaloyl chloride (0.9 mL, 10 mmol) dropwise at room temperature under nitrogen atmosphere and the stirring was continued for ½ an hour. The reaction mixture was cooled to −40° C., was added solution of I$_2$ (1.2 gm, 4.85 mmol) in pyridine: H$_2$O (8 mL; 9.75:0.25) over 15 min and stirred for 1 h. The reaction mixture was quenched by using aq. Na$_2$S$_2$O$_3$.5H$_2$O solution (200 mL, 1M). The reaction mixture was diluted with H$_2$O (200 mL) and extracted using DCM (300 mL*2). The separated organic layers were dried over anhydrous sodium sulphate, filtered and concentrated under reduced pressure. The crude product purified on flash silica using MeOH-DCM+1% Et$_3$N (4:96) as eluent to give pure compound 15 (2.5 g, 86%) as a dense liquid. Similarly α-H-phosphonate 12 was reacted with 14A under identical conditions to give 15A in 69% yield.

Example 12: Synthesis of Compound 16 and 16A 6-(Carbobenzyloxy)aminohexyl (2-azido-3,6-di-O-benzyl-2-deoxy-α-D-glucopyranosyl phosphate)-(1→4)-2-azido-3,6-di-O-benzyl-2-deoxy-α-D-glucopyranoside, triethylammonium salt (16) and 6-(Carbobenzyloxy)aminohexyl (2-azido-3,6-di-O-benzyl-2-deoxy-α-D-glucopyranosyl phosphate)-(1→4)-2-azido-3,6-di-O-benzyl-2-deoxy-β-D-glucopyranoside, triethylammonium salt (16A)

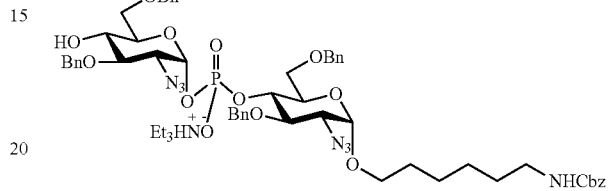

A solution of dimer compound 15 (2.5 g, 2.04 mmol) in 0.25 M CH$_3$ONa in methanol (25 mL) was allowed to stir at 55° C. for 1.5 h. The reaction mixture was cooled to room temperature and neutralized with Amberlite IR-120 (H$^+$) resin, filtered through the Whatman filter paper and concentrated. The crude product purified on flash silica using MeOH-DCM+1% Et$_3$N (4:96) as eluent to give pure compound 16 as a brown syrup (2.4 g, quantitative). Similarly compound 15A is allowed react with sodium methoxide under identical conditions to get compound 16A in 78% yield.

Example 13: Synthesis of Compound 17 and 17A 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, bis-triethylammonium salt (17) and 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-β-D-glucopyranoside, bis-triethylammonium salt (17A)

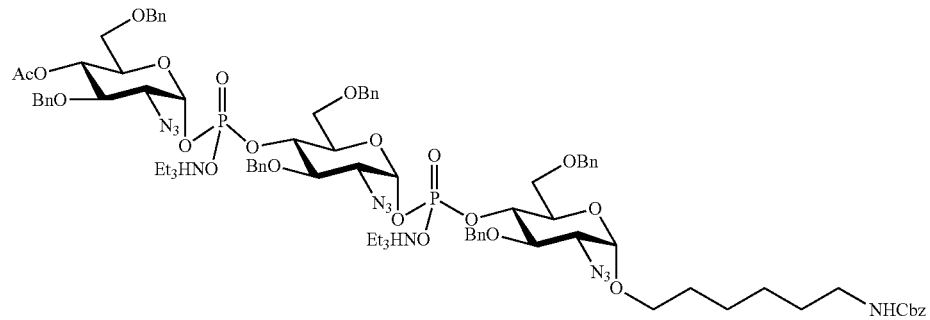

The mixture of α-H-phosphonate 12 (2.55 gm, 4.29 mmol) and alcohol 14 (1.7 gm, 1.43 mmol) were coevaporated with anhydrous pyridine under vacuum for three times. The residue was dissolved in anhydrous pyridine (40 mL) and was added pivaloyl chloride (1.07 mL, 8.58 mmol) dropwise over 10 min. at room temperature stirred for 30 min. The reaction mixture was cooled to −40° C. and was added solution of $I_2$ (2.1 gm, 8.58 mmol, 6 eq.) in pyridine:water (9.75:0.25, 10 mL) over 15 min. The cooling stopped and the reaction mixture left to stir for additional 1 h. The reaction was quenched by addition of saturated solution of $Na_2S_2O_3.5H_2O$ (50 mL). The reaction mixture was cooled to room temperature, diluted with water (100 mL) and extracted by DCM (400 mL) for two times. The separated organic layers were dried over anhydrous sodium sulphate, filtered and concentrated under reduced pressure. The residue was purified by flash silicagel column chromatography using MeOH-DCM+1% $Et_3N$ (5:96) as eluent, furnished compound 17 as yellow syrup (1.5 g, 60%). Similarly 17A is prepared by reacting α-H-phosphonate 12 with 16A under identical conditions in 88% yield.

Example 14: Synthesis of Compound 18 and 18A 6-(Carbobenzyloxy)aminohexyl (2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, bis-triethylammonium salt (18) and 6-(Carbobenzyloxy)aminohexyl (2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, bis-triethylammonium salt (18A)

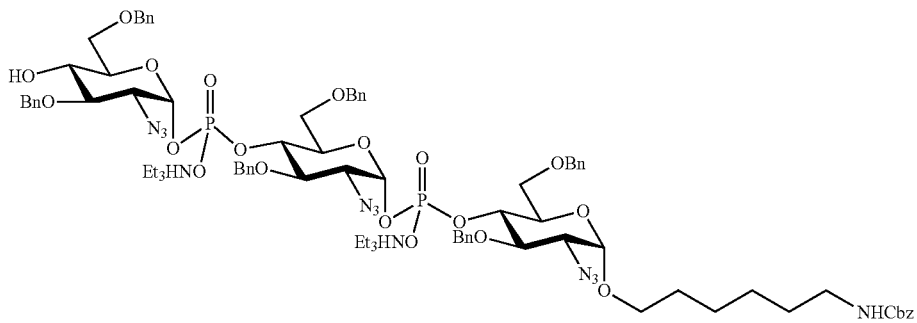

A solution of trimer compound 17 (1.5 g, 0.85 mmol) in 0.25 M $CH_3ONa$ in methanol (20 mL) was allowed to stir at 55-60° C. for 2 h. The reaction mixture was cooled to room temperature, diluted with methanol (20 mL) and neutralized with Amberlite IR-120 ($H^+$) resin, filtered through the Whatman filter paper and concentrated. The crude product purified on flash silica using MeOH-DCM+1% $Et_3N$ (5:96) as eluent to give pure compound 18 as a yellow dense syrup (1.3 gm, 89%). Similarly compound 18A prepared by reacting with sodium methoxide under identical conditions in 69% yield.

Example 15: Synthesis of Compound 19 and 19A 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, tris-triethylammonium salt (19) and 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-β-D-glucopyranoside, tris-triethylammonium salt (19A)

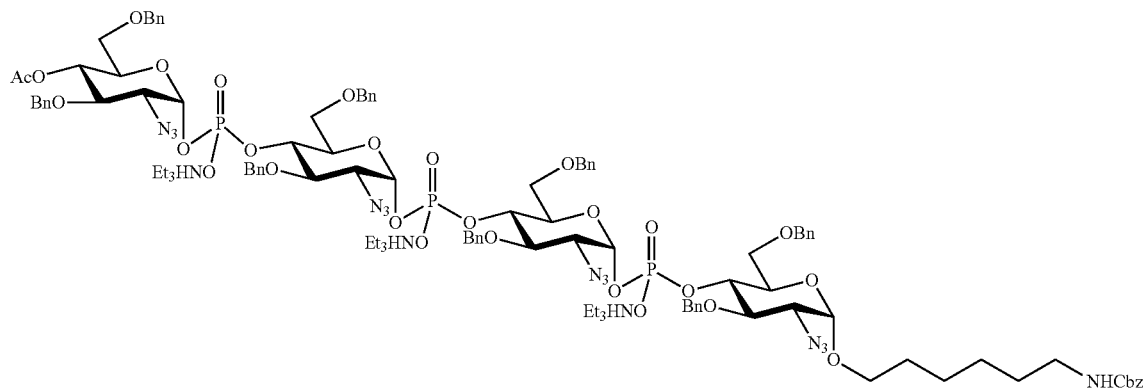

The mixture of trimer hydroxyl compound 18 (1.3 gm, 0.75 mmol) and α-H-phosphonate 12 (1.3 gm, 2.25 mmol) were coevaporated with anhydrous pyridine under vacuum for three times. The mixture was dissolved in anhydrous pyridine (30 mL) and was added pivaloyl chloride (0.65 mL, 5.25 mmol) dropwise over 10 min at room temperature under inert atmosphere. The reaction mixture was left to stir for 30 min. The reaction mixture was cooled to −40° C. and was added solution of $I_2$ (1.3 gm, 5.25 mmol) in pyridine: water (9.75:0.25, 3 mL) over 15 min. The cooling stopped and the reaction mixture left to stir for additional 1 h. The reaction was quenched by addition of saturated solution of $Na_2S_2O_3.5H_2O$ (50 mL). The reaction mixture was cooled to room temperature, diluted with water (100 mL) and extracted by DCM (200 mL) for two times. The separated organic layers were dried over anhydrous sodium sulphate, filtered and concentrated under reduced pressure. The residue was purified by flash silica gel column chromatography using MeOH-DCM+1% $Et_3N$ (5:95) as eluent, furnished compound 19 as a yellow semisolid (0.9 g, 53%). Similarly compound 18A was reacted with α-H-phosphonate 12 under identical conditions to prepare compound 19A with 80% yield.

Example 16: Synthesis of Compound Men X Tetramer 1 and 1A 6-(Carbobenzyloxy)aminohexyl (4-O-acetyl-2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-2-acetamido-3,6-di-O-benzyl-2-deoxy-α-D-glucopyranoside, tris-triethylammonium salt (1) and 6-(Carbobenzyloxy)aminohexyl (4-O-acetyl-2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-2-acetamido-3,6-di-O-benzyl-2-deoxy-β-D-glucopyranoside, tris-triethylammonium salt (1A)

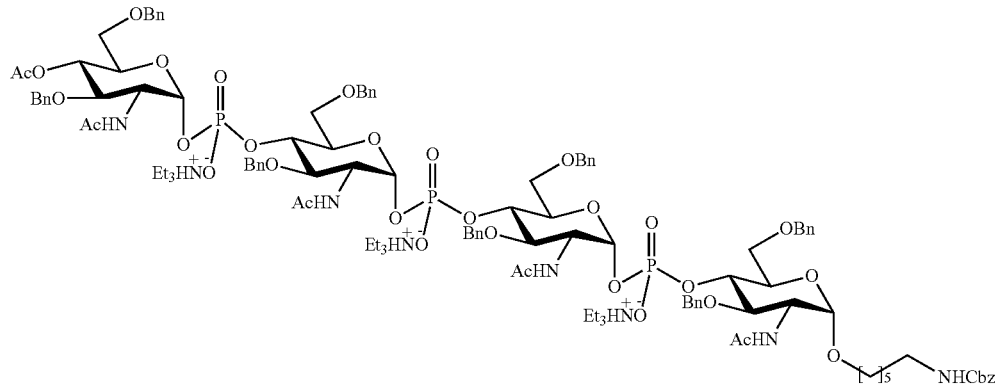

To the stirred solution of tetramer azide compound 19 (0.9 g, 0.4 mmol) in anhydrous pyridine (10 mL) was added thioacetic acid (3.2 mL, excess) dropwise over 10 min at room temperature under inert atmosphere. The reaction mixture was stirred at the same temperature for overnight. After completion of reaction (monitored by TLC), the reaction mixture was diluted with cold water (30 mL) followed by saturated solution of sodium bicarbonate (20 mL). The reaction mixture was extracted by (70 mL) DCM for two times. The separated organics were dried over anhydrous sodium sulphate, filtered and concentrated under reduced pressure. The residue was diluted by minimum volume of DCM (4 mL) then pet ether (40 mL) was added which resulted in to solid precipitation of product. The organic layer was decanted the residue was purified by column chromatography using 5-10% MeOH:DCM+1% TEA as an eluent to afford the N-acetyl tetramer compound as brown semi solid. Isolated yield: 600 mg, 45%. Similarly compound 19A reacted with thioacetic acid in pyridine under identical conditions to obtain the compound with NHAC in place of $N_3$ in 40% yield.

6-(Carbobenzyloxy)aminohexyl (2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-2-acetamido-3,6-di-O-benzyl-2-deoxy-α-D-glucopyranoside, tris-triethylammonium salt 6-(Carbobenzyloxy)aminohexyl (2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-(2-acetamido-3,6-di-O-benzyl-2-deoxy-α-D-glucopyranosyl phosphate)-(1→4)-2-acetamido-3,6-di-O-benzyl-2-deoxy-β-D-glucopyranoside, tris-triethylammonium salt

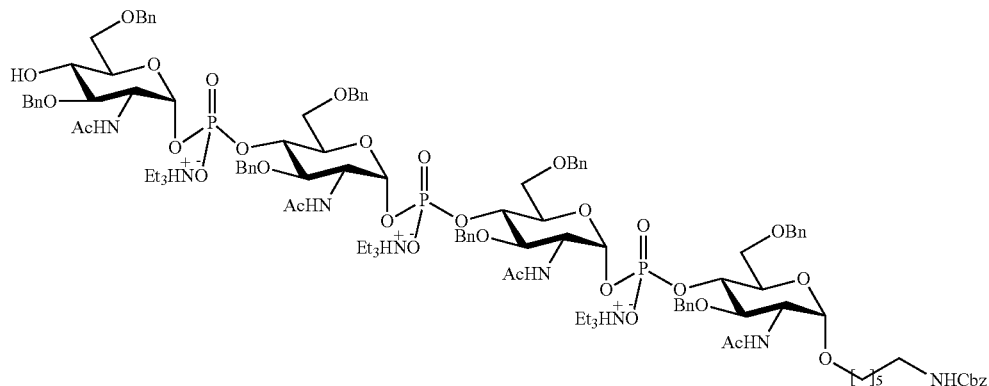

To the stirred solution of N-acetyl tetramer from above step (600 mg, 0.253 mmol) in anhydrous methanol (20 mL) was added NaOMe (600 mg Excess) portion-wise over 5 min. under nitrogen atmosphere. The reaction mixture was heated to 60° C. for 1.5 h. The reaction mixture was cooled to room and neutralized using Amberlite IR-120 resin. The reaction mixture was filtered through the Whatman filter paper and the residue washed 2-3 times using methanol (50 mL). The collected filtrates concentrated under reduced pressure. The crude reaction mass purified by flash gel column using 10% MeOH:DCM+1% TEA as an eluent to afford the tetramer hydroxy compound (500 mg, 84%). Under similar conditions tetramer with beta linker is deacetylated with 76% yield.

6-Aminohexyl (2-acetamido-2-deoxy-α-D-glucopyranosyl phosphate)-(1→4)-(2-acetamido-2-deoxy-α-D-glucopyranosyl phosphate)-(1→4)-(2-acetamido-2-deoxy-α-D-glucopyranosyl phosphate)-(1→4)-2-acetamido-2-deoxy-α-D-glucopyranoside, tris-sodium salt (Men X Tetramer 1) and 6-Aminohexyl (2-acetamido-2-deoxy-α-D-glucopyranosyl phosphate)-(1→4)-(2-acetamido-2-deoxy-α-D-glucopyranosyl phosphate)-(1→4)-(2-acetamido-2-deoxy-α-D-glucopyranosyl phosphate)-(1→4)-2-acetamido-2-deoxy-β-D-glucopyranoside, tris-sodium salt (Men X Tetramer 1A)

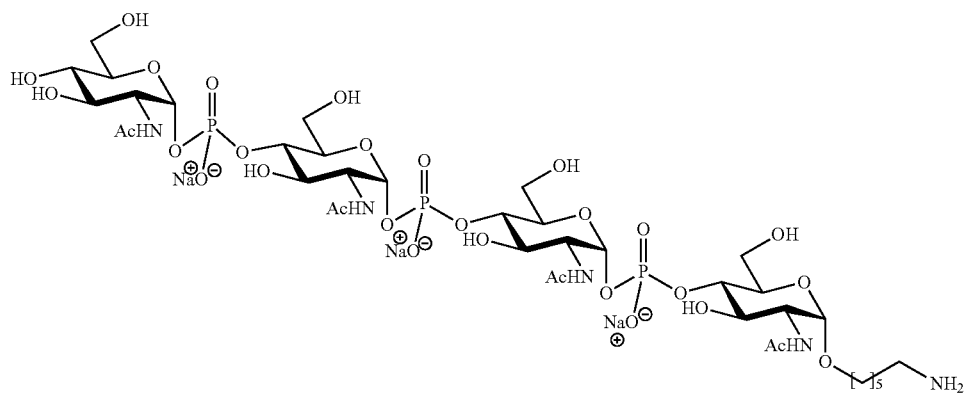

To the solution of tetramer hydroxy prepared in the above step (300 mg, 0.128 mmol) in methanol:water, 1:1 (30 mL) was added Pd(OH)$_2$/C (20 mol %, 600 mg) under inert atmosphere at room temperature. The reaction mixture was left to stir at 104 psi for 15 h under hydrogen atmosphere. After completion of reaction (monitored by TLC), the reaction mixture was filtered through the celite bed. The celite bed was washed by 30 mL of H$_2$O for three times. The separated filtrate was concentrated under reduced pressure. The crude mass was purified by solvent treatment. The residue was washed by DCM followed by cold methanol (5 mL*2) times. White solid compound obtained. Isolated Yield: 120 mg, 86%, HPSEC purity: 98%. Exact Mass: 1235.84. Observed mass (M-Na)$^-$ 1212.34.

IR: 3436, 2517, 1632, 1383, 1443, 1204.

$^1$H NMR (500 MHz, D$_2$O) δ 5.55-5.44 (m, 3H), 4.10-3.96 (m, 4H), 3.96-3.83 (m, 11H), 3.82-3.56 (m, 12H), 3.50 (t, J=9.8 Hz, 1H), 3.45-3.42 (m, 1H), 2.93 (s, 2H), 2.10-1.92 (m, 12H), 1.69-1.48 (m, 4H), 1.43-1.27 (m, 4H).

$^{13}$C NMR (126 MHz, D$_2$O) δ 174.5, 174.4, 174.2, 171.0, 96.4, 94.4, 94.3, 94.1, 94.0, 74.4, 74.3, 73.8, 73.7, 73.0, 72.0, 71.2, 70.8, 70.7, 70.1, 69.9, 69.4, 68.0, 60.3, 60.2, 60.0, 53.7, 53.6, 53.5, 53.4, 39.4, 28.2, 26.7, 25.3, 24.8, 22.1, 22.0, 21.8.

6-Aminohexyl (2-acetamido-2-deoxy-α-D-glucopyranosyl phosphate)-(1→4)-(2-acetamido-2-deoxy-α-D-glucopyranosyl phosphate)-(1→4)-(2-acetamido-2-deoxy-α-D-glucopyranosyl phosphate)-(1→4)-2-acetamido-2-deoxy-α-D-glucopyranoside, tris-sodium salt (Men X Tetramer 1)

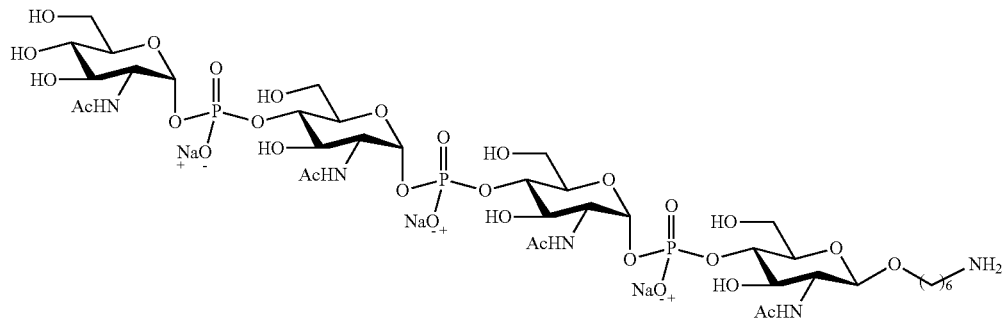

1A

To the solution of Tetramer hydroxy (100 mg, 0.042 mmol) in methanol:water, 7:3 (30 mL) was added Pd(OH)$_2$/C (20 mol %) under inert atmosphere at room temperature. The reaction mixture was left to stir at 60 psi for 6 h under hydrogen atmosphere. After completion of reaction (monitored by TLC), the reaction mixture was filtered through the celite bed. The celite bed was washed by 30 mL of H$_2$O for three times. The separated filtrate was concentrated under reduced pressure. The crude mass was purified by solvent treatment. The residue was washed by DCM followed by cold methanol (5 mL*2) times. The pure product was then subjected to Na ion exchange by reacting it with Dowex 50W Na$^+$ form (2 g) in water (5 mL) for 6 h at rt. Then the reaction mass filtered through the Whatmann filter paper. The filtrate was concentrated under reduced pressure. The crude mass dried under vacuum for 2 h provided the white solid compound. Exact Mass: 1235.28; Isolated Yield: 38 mg, 71%, HPSEC purity: 98%.

IR: 3434, 2067, 1634, 1383, 1221, 1043.

$^1$H NMR (500 MHz, D$_2$O): δH 5.41 (bs, 3H), 4.39 (bs, 1H), 3.63-3.91 (m, 26H), 3.43 (bs, 4H), 2.86 (bs, 2H), 1.94 (s, 12H), 1.45-1.53 (m, 4H), 1.25 (bs, 4H).

$^{13}$C NMR (126 MHz, D$_2$O): δc 177, 103.6, 96.9, 96.8, 96.6, 77.4, 76.7, 76.3, 75.4, 74.5, 73.2, 72.8, 72.5, 71.9, 62.9, 62.7, 62.5, 57.9, 55.9-56.2, 41.9, 30.8, 29.1, 27.7, 27, 24.5.

Analytical Test:

Determination of Antigenic Properties of Oligomer and Conjugates Prepared Using Synthetic Men-X Tetramer (Men-X Tetramer-TT Conjugate)

The antigenicity of synthetic Men-X tetramer and its conjugate with tetanus toxoid (Men-X tetramer-TT conjugate) was compared with bacterial polysaccharide in relation to a no-antigen control in a competition enzyme-linked immunosorbent assay (ELISA). In this assay, eight thousand fold diluted rabbit antiserum against N. meningitidis serogroup X (228801; BD) was incubated for 1 hour at 37° C. with different antigens (i.e. bacterial polysaccharide, Men-X tetramers (1 and 1A) and conjugate prepared using synthetic Men-X tetramers (1-TT, and 1A-TT) at 10-1000 µg oligosaccharide/ml diluted in phosphate-buffered saline containing 0.1% v/v Brij 35 and 5% FBS; in 96 well micro titer plate (Plate A). A separate plate (plate B) was coated with a mixture of Men-X bacterial polysaccharide (PS) and methylated-Human Serum Albumin (m-HSA) and subsequently blocked with 5% FBS after overnight incubation at 2-8° C. To this plate B, antiserum-antigen mix from plate A was added and incubated for 1 hour at 37° C. and 1 hour at room temperature. The plate was washed with phosphate-buffered saline, pH 7.4 containing 0.1% Brij 35. The plate was incubated for 60 minutes at room temperature with peroxidase labelled anti-rabbit IgG antibodies in PBS, 0.1% Brij 35 and 5% FBS. Plate was washed again and incubated for 10 minute at room temperature with the 100 µl peroxidase substrate, 3,3',5,5'-tetramethylbenzidine-H$_2$O$_2$ in sodium acetate buffer. The reaction was stopped by adding 50 µl of 2 M H$_2$SO$_4$. The A$_{450}$ was recorded on an ELISA reader (Tecan micro plate reader). The percentage inhibition of the antibodies in the antiserum by each antigen was calculated as below:

$$\text{Inhibition \%} = (OD_{NAC} - OD_A)/(OD_{NAC} - OD_B) \times 100$$

Where, OD$_{NAC}$ is optical density for no antigen control, OD$_B$ is the optical density of blank wells. Optical density for test antigens (Men-X tetramer and Men-X tetramer-TT conjugate) and positive control is referred as OD$_A$. The data for alpha anomer (1) are presented as the mean±SD of the measurements performed in triplicate in the FIG. 1, similar data were observed for the beta anomer (1A).

The inhibition ELISA results showed the antigenicity of synthetic Men X tetramer based TT conjugates in comparison to the 'No antigen control'. As shown in FIG. 1; synthetic Men-X tetramer and its TT conjugates were able to neutralize the antibodies specific to *N. meningitidis* serogroup X polysaccharide present in the antiserum to a significant extent (up to 68 and 89% respectively) and inhibited the binding of antibodies to the bacterial Men-X polysaccharide coated on plate.

We claim:

1. Novel process of synthesizing oligomers of *Neisseria meningitidis* serogroup X of chemical formula where n is 3 to 5, said process comprising the steps of:

synthesizing hemiacetal compound (10), wherein compound (10) is 4-O-acetyl-2-azido-3,6-di-O-benzyl-2-deoxy-α,β-D-glucopyranose subjecting said hemiacetal compound (10) to phosphitylating reagent to obtain compound (11) which is subjected to anomerization to obtain propagation unit (12), wherein compound (11) is and propagation unit (12) is 4-O-Acetyl-2-azido-3,6-di-O-benzyl-2-deoxy-α-D-glucopyranosyl hydrogenphosphonate synthesizing terminal unit(s) (14) and (14A),
wherein terminal unit (compound 14) is 6-(Benzyloxycarbonyl)aminohexyl 2-deoxy-α-D-glucopyranoside and wherein terminal unit (compound 14A) is 6-(Benzyloxycarbonyl)aminohexyl 2-azido-3,6-di-O-benzyl-2-deoxy-β-D-glucopyranoside coupling said propagation unit (12) with said terminal unit (14) and coupling said propagation unit (12) with said terminal unit (14A), wherein a molar ratio of compound (12) to compound (14) and compound (14A) is 1:2, in the presence of coupling reagents to obtain a yield in the range of 86% to 90% of compound (15) and (15A) respectively, wherein compound (15) is 6-(Carbobenzyloxy)aminohexyl (4-O-acetyl-2-azido-3,6-di-O-benzyl-2-deoxy-α-D-glucopyranosyl phosphate)-(1→4)-2-azido-3,6-di-O-benzyl-2-deoxy-α-D-glucopyranoside, triethylammonium salt and compound (15A) is 6-(Carbobenzyloxy)aminohexyl (4-O-acetyl-2-azido-3,6-di-O-benzyl-2-deoxy-α-D-glucopyranosyl phosphate)-(1→4)-2-azido-3,6-di-O-benzyl-2-deoxy-β-D-glucopyranoside, triethylammonium salt reacting said compounds (15) and (15A) with deacetylating reagents to obtain dimeric compounds (16) and (16A), wherein compound (16) is 6-(Carbobenzyloxy)aminohexyl (2-azido-3,6-di-O-benzyl-2-deoxy-α-D-glucopyranosyl phosphate)-(1→4)-2-azido-3,6-di-O-benzyl-2-deoxy-α-D-glucopyranoside, triethylammonium salt and compound (16A) is 6-(Carbobenzyloxy)aminohexyl (2-azido-3,6-di-O-benzyl-2-deoxy-α-D-glucopyranosyl phosphate)-(1→4)-2-azido-3,6-di-O-benzyl-2-deoxy-β-D-glucopyranoside, triethylammonium salt

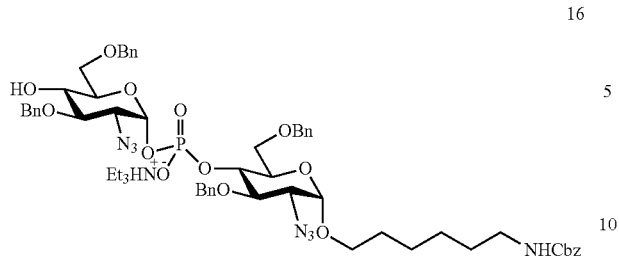

16

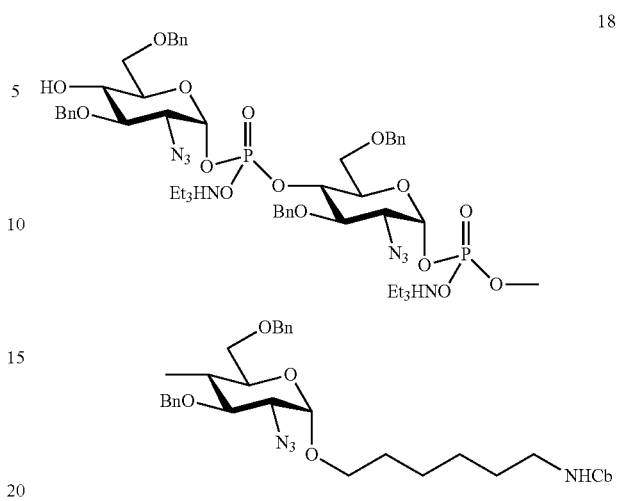

18 coupling compound (16) to said propagation unit (12) and compound (16A) to said propagation unit (12), wherein a molar ratio of compound (12) to compound (16) and (16A) is 1:3, using said coupling reagents to obtain trimer compounds (17) and (17A) with a yield in the range of 60% to 70%, wherein compound (17) is 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, bis-triethylammonium salt and compound (17A) is 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-β-D-glucopyranoside, bis-triethylammonium salt

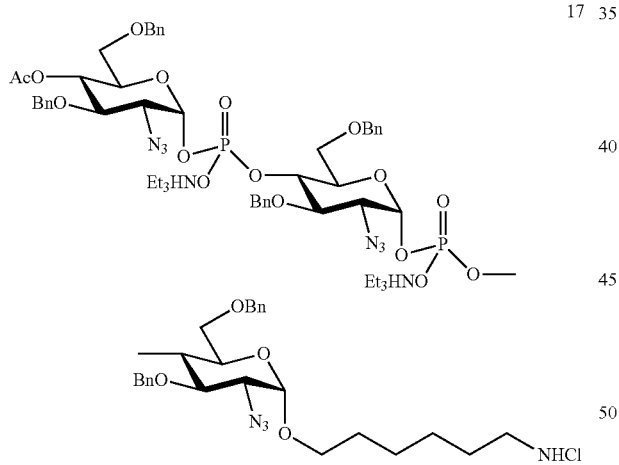

17 reacting said compounds (17) and (17A) with deacetylating reagents to obtain triimeric compounds (18) and (18A), wherein compound (18) is 6-(Carbobenzyloxy)aminohexyl (2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, bis-triethylammonium salt and oligomer (18A) is 6-(Carbobenzyloxy)aminohexyl (2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-β-D-glucopyranoside, bis-triethylammonium salt coupling said compound (18) to said propagation unit (12) and said compound (18A) to said propagation unit (12), wherein a molar ratio of compound (12) to compound (18) and compound (18A) is 1:3, using said coupling reagents to obtain tetramer compounds (19) and (19A), with yield in the range of 53% to 58% wherein compound (19) is 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-α-D-glucopyranoside, tris-triethylammonium salt and oligomer (19A) is 6-(Carbobenzyloxy)aminohexyl (4-O-acetyl-2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-(2-azido-3,6-di-O-benzyl-2-deoxy-α-D-glucopyranosyl phosphate)-(1→4)-2-azido-3,6-di-O-benzyl-2-deoxy-β-D-glucopyranoside, tris-triethylammonium salt

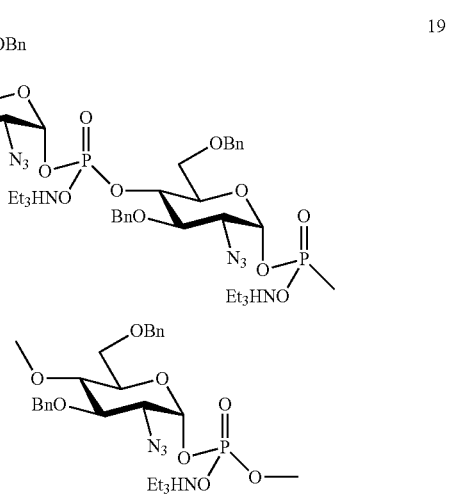

19

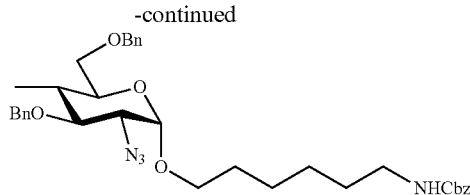

5 optionally performing iterative reactions in the presence of said deacetylating reagents and said coupling reagents to yield a pentamer or hexamer, performing one step reduction by reductive N-acetylating reagent, deacetylation using said deacetylating reagents and final deprotection of benzyl and Cbz by hydrogenation, wherein said process results in novel higher synthetic oligomers with high yield capable of being used for the development of a conjugate vaccine against meningococcal serogroup X infection.

2. The novel process of synthesizing oligomers as claimed in claim 1 wherein said novel higher synthetic oligomers are tetramers.

3. The novel process of synthesizing oligomers as claimed in claim 1 wherein the overall reaction time taken to synthesize said oligomers is in the range of 225 hours to 276 hours.

4. The novel process of synthesizing oligomers as claimed in claim 1 wherein said hemiacetal compound (10) is synthesized by:

a. subjecting sugar of compound (2) to diazotransfer reagent and then acetylation in the presence of pyridine to obtain compound (3), wherein compound (2) is D-(+)-Glucosamine hydrochloride

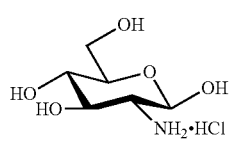

2 and compound (3) is 1,3,4,6-Tetra-O-acetyl-2-azido-2-deoxy-D-glucopyranose

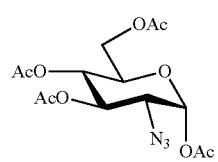

3 b. reacting compound (3) with donor group at a temperature ranging from 0° C. to room temperature to obtain compound (4), wherein compound (4) is 4-Methylphenyl 3,4,6-tri-O-acetyl-2-azido-2-deoxy-1-thio-α,β-D-glucopyranoside

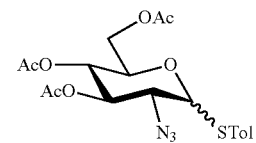

4 c. reacting compound (4) with deacetylating reagent in organic solvent at a temperature ranging from 0° C. to room temperature to obtain compound (5), wherein compound (5) is 4-Methylphenyl 2-azido-2-deoxy-1-thio-α,β-D-glucopyranoside

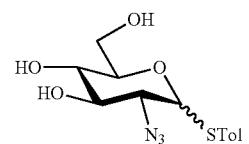

5 d. subjecting compound (5) to benzylidene protection at room temperature resulting in compound (6), wherein compound (6) is 4-Methylphenyl 2-azido-4,6-O-benzylidene-2-deoxy-1-thio-α,β-D-glucopyranoside

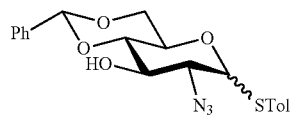

6 e. subjecting compound (6) to benzyl protection at room temperature to obtain compound (7), wherein compound (7) is 4-Methylphenyl 2-azido-4,6-O-benzylidene-3-O-benzyl-2-deoxy-1-thio-α,β-D-glucopyranoside

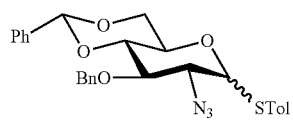

7 f. subjecting compound (7) to regioselective benzylidine ring opening reagents at 0° C. to obtain compound (8) which is subjected to acylating reagents at 0° C. to obtain compound (9), wherein compound (8) is 4-Methylphenyl 2-azido-3,6-di-O-benzyl-2-deoxy-1-thio-α,β-D-glucopyranoside

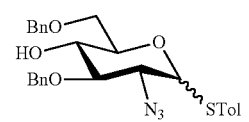

8 and compound (9) is 4-Methylphenyl 4-O-acetyl-2-azido-3,6-di-O-benzyl-2-deoxy-1-thio-α,β-D-glucopyranoside

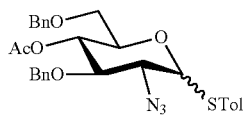

9 g. subjecting compound (9) to thiotolyl deprotection at a temperature ranging from 0° C. to room temperature to obtain hemiacetal compound (10).

5. The novel process of synthesizing oligomers as claimed in claim 1 wherein said termination unit (14, 14A) is synthesized by
  subjecting compound 9 to glycosidation reaction resulting in attachment of linker to obtain compound 13, wherein compound 9 is 4-Methylphenyl 4-O-acetyl-2-azido-3,6-di-O-benzyl-2-deoxy-1-thio-α,β-D-glucopyranoside

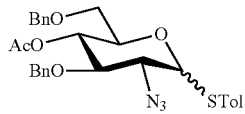

9 and compound 13 is

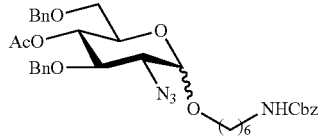

13 reacting said compound 13 with deacetylating reagents and subjecting to purification by known process to obtain compound 14 and 14A.

6. The novel process of synthesizing oligomers as claimed in claim 1 wherein said coupling reagents are selected from Pivaloyl chloride in presence of pyridine and 1-Adamantanecarbonyl chloride.

7. The novel process of synthesizing oligomers as claimed in claim 1 wherein said deacetylating reagents are selected from Sodium Methoxide and Sodium ethoxide.

8. The novel process of synthesizing oligomers as claimed in claim 1 wherein said final deprotecting reagents are selected from $Pd(OH)_2$—$H_2$, Pd over carbon-$H_2$.

9. The novel process of synthesizing oligomers as claimed in claim 4 wherein said diazotransfer reagent is selected from 1H-imidazole-1-sulfonyl azide and trifluoromethanesulfonyl azide (TfN3).

10. The novel process of synthesizing oligomers as claimed in claim 4 wherein said benzylidene protection is obtained by reacting with reagents selected from benzaldehyde dimethyl acetal [$PhCH(OMe)_2$] and benzaldehyde.

11. The novel process of synthesizing oligomers as claimed in claim 4 wherein said benzyl protection is obtained by reacting with reagents selected from benzyl bromide and sodium hydroxide.

12. The novel process of synthesizing oligomers as claimed in claim 4 wherein the said regioselective ring opening reagent is selected from combination of Triethyl Silane ($Et_3SiH$), Boron trifluoride diethyl etherate $BF_3.OEt_2$), Borane tetrahydrofuran complex ($BH_3.THF$) and copper triflate $Cu(OTf)_2$.

13. The novel process of synthesizing oligomers as claimed in claim 4 wherein said acylation reagent is Acetic Anhydride ($Ac_2O$) in pyridine or 4-Dimethylaminopyridine (DMAP).

14. The novel process of synthesizing oligomers as claimed in claim 4 wherein said thiotolyl deprotection is obtained by reacting with reagents selected from N-Bromosuccinimide (NBS), N-Iodosuccinimide (NIS), and Silver triflate (AgOTf) in an equimolar ratio.

15. The novel process of synthesizing oligomers as claimed in claim 1 wherein said phosphitylating agent is selected from Di-phenyl phosphite pyridine, phosphorous trichloride, imidazole, salicylchlorophosphite, and phosphorous acid.

16. The novel process of synthesizing oligomers as claimed in claim 1 wherein said novel higher synthetic oligomers are selected from the group consisting of oligomers (18, 18A, 19, 19A, 1, and 1A),
  wherein oligomer (1) is 6-Aminohexyl (2-acetamido-2-deoxy-α-D-glucopyranosyl phosphate)-(1→4)-(2-acetamido-2-deoxy-α-D-glucopyranosyl phosphate)-(1→4)-(2-acetamido-2-deoxy-α-D-glucopyranosyl phosphate)-(1→4)-2-acetamido-2-deoxy-α-D-glucopyranoside, tris-sodium salt and oligomer (1A) is 6-Aminohexyl (2-acetamido-2-deoxy-α-D-glucopyranosyl phosphate)-(1→4)-(2-acetamido-2-deoxy-α-D-glucopyranosyl phosphate)-(1→4)-(2-acetamido-2-deoxy-α-D-glucopyranosyl phosphate)-(1→4)-2-acetamido-2-deoxy-β-D-glucopyranoside, tris-sodium salt

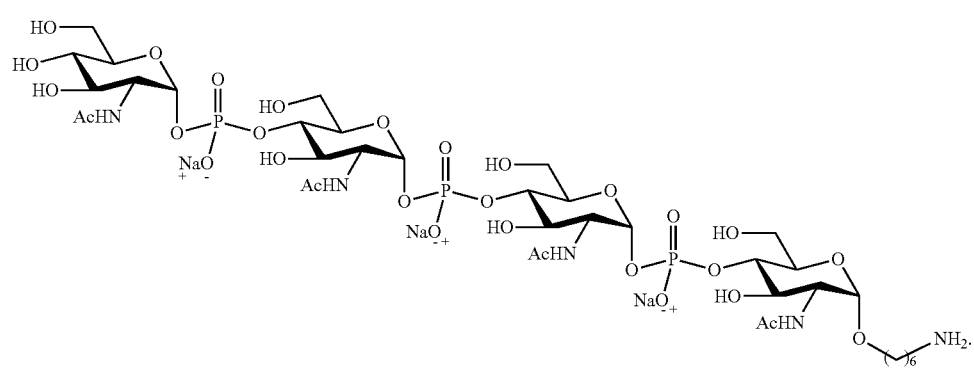

1

17. The novel process of synthesizing oligomers as claimed in claim 16 wherein time required for said final deprotection by hydrogenation for compound (1) is 10 hours to 15 hours and for compound (1A) is 6 hours to 8 hours.

18. The novel process of synthesizing oligomers as claimed in claim 16 wherein the overall reaction time taken to synthesize said oligomers (1) and (1A) is 257 hours.

19. The novel process of synthesizing oligomers as claimed in claim 1, wherein the steps of coupling said propagation unit (12) with said terminal unit (14) and coupling said propagation unit (12) with said terminal unit (14A) is performed in the presence of coupling reagents at room temperature for 30 minutes followed by oxidation using iodine at −40° C. in pyridine:water at a ratio of 9.75:0.25 for 1.5 hours.

* * * * *